United States Patent
Herron et al.

(10) Patent No.: US 7,811,754 B2
(45) Date of Patent: Oct. 12, 2010

(54) DETECTION OF SINGLE NUCLEOTIDE POLYMORPHISMS USING PLANAR WAVEGUIDES

(75) Inventors: James N. Herron, Salt Lake City, UT (US); Samuel Tolley, Salt Lake City, UT (US); Hsu-Kun Wang, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 789 days.

(21) Appl. No.: 10/941,289

(22) Filed: Sep. 9, 2004

(65) Prior Publication Data

US 2006/0228713 A1  Oct. 12, 2006

Related U.S. Application Data

(63) Continuation of application No. PCT/US03/01600, filed on Jan. 17, 2003.

(60) Provisional application No. 60/350,633, filed on Jan. 18, 2002.

(51) Int. Cl.
*C12Q 1/68* (2006.01)
*C12P 19/34* (2006.01)
*C07H 21/02* (2006.01)
*C07H 21/04* (2006.01)
*C07H 21/00* (2006.01)

(52) U.S. Cl. .......................... 435/6; 435/91.1; 435/91.2; 536/23.1; 536/24.3; 536/24.33; 536/25.3; 536/25.32

(58) Field of Classification Search ............... 435/6, 435/91.1, 183, 283.1, 287.1, 287.2, 91.2; 436/94, 501; 536/231, 24.3, 24.33, 25.3, 536/25.32
See application file for complete search history.

(56) References Cited

U.S. PATENT DOCUMENTS

| | | | |
|---|---|---|---|
| 4,775,637 A | 10/1988 | Sutherland et al. | |
| 4,849,340 A | 7/1989 | Oberhardt | |
| 5,512,492 A | 4/1996 | Herron et al. | |
| 5,599,668 A | 2/1997 | Stimpson et al. | |
| 5,846,842 A | 12/1998 | Herron et al. | |
| 6,340,598 B1 | 1/2002 | Herron et al. | |

FOREIGN PATENT DOCUMENTS

WO   WO 99/47705   9/1999

OTHER PUBLICATIONS

Budach et al., Planar Waveguides as High-Performance Sensing Platforms for Fluorescence-Based Multiplexed Oligonucleotide Hybridization Assays. Anal. Chem., 71, 3347-3355, 1999.*

Koval et al., Real-Time Oligonucleotide Hybridization Kinetics Monitored by Resonant Mirror Technique, IUBMB Life, 48, 317-320, 1999.*

Peter et al., Optical DNA-sensor chip for real-time detection of hybridization events. Fresenius J. Anal. Chem., 371, 120-127, 2001.*

2,473,558, Mar. 27, 2008, CIPO Office Action.

Supplementary European Search Report, dated Dec. 1, 2006 (5 pages).

Stimpson et al., "The Utility of Optical Waveguide DNA Array Hybridization and Melting for Rapid Resolution of Mismatches, and for Detection of Minor Mutant Components in the Presence of a Majority of Wild Type Sequence: Statistical Model and Supporting Data," Genetic Analysis: Biomolecular Engineering vol. 13, No. 3 (Sep. 1996), pp. 73-80.

Donger et al., "KVLQTI C-Terminal Missense Mutation Causes a Forme Fruste Long-QT Syndrome," Circulation, vol. 96, No. 9 (Nov. 4, 1997), pp. 2778-2781.

Nilsson et al., "Detection of Mutations in PCR Products from Clinical Samples by Surface Plasmon Resonance," Journal of Molecular Recognition, vol. 10, No. 1 (1997), pp. 7-17.

Nilsson et al., "Real-Time Monitoring of DNA Manipulations Using Biosensor Technology," Analytical Biochemistry, vol. 224, No. 1 (Jan. 1, 1995), pp. 400-408.

Schneider et al., "Hartman Interferometer: Versatile Integrated Optic Sensor for Label-Free, Real-Time Quantification of Nucleic Acids, Proteins, and Pathogens," Clinical Chemistry, vol. 43, No. 9 (1997) pp. 1757-1763.

Peter et al., "Optical DNA-Sensor Chip for Real-Time Detection of Hybridization Events," Fresenius Journal of Analtytical Chemistry, vol. 371, No. 2 (Sep. 2001), pp. 120-127.

Abel et al, "Fiber-Optic Evanescent Wave Biosensor for the Detection of Oligonucleotides," Analytical Chemistry, vol. 68, No. 17 (Sep. 1, 1996), pp. 2905-2912.

Tolley et al., "Single-Chain Polymorphism Analysis in Long QT Syndrome Using Planar Waveguide Fluorescent Biosensors," Analytical Biochemistry, vol. 315, No. 2 (Apr. 15, 2003), pp. 223-237.

* cited by examiner

*Primary Examiner*—Frank W Lu
(74) *Attorney, Agent, or Firm*—Ballard Spahr LLP

(57) ABSTRACT

Methods and apparatus for detecting single nucleotide polymorphisms in genes of interest are disclosed. A plurality of probes is immobilized on a planar waveguide. The probes comprise sequences complementary to a wildtype sequence of the gene of interest and complementary to a sequence of a known SNP in the gene of interest. A fluorescently-labeled analyte is flowed over the planar waveguide. The binding between the labeled analyte and each of the probes causes a change in the fluorescence signal. The SNP is detected by comparing the hybridization kinetics of the analyte with each of the probes. A method of detecting single nucleotide polymorphisms in a gene of interest by sequencing by hybridization is also disclosed.

8 Claims, 12 Drawing Sheets

DETECTION OF SINGLE NUCLEOTIDE POLYMORPHISMS USING PLANAR WAVEGUIDES

CROSS-REFERENCE TO RELATED APPLICATION

This application is a continuation of PCT Application No. PCT/US03/01600 filed Jan. 17, 2003, which claims the benefit of priority under 35 U.S.C. §119(e) to U.S. Provisional Application Ser. No. 60/350,633, filed Jan. 18, 2002, the disclosure of which is hereby incorporated herein in its entirety by this reference.

U.S. GOVERNMENT LICENSE RIGHTS

The research supporting this invention was partially funded by National Institute of Health Grant HL32132. The United States Government may have some right in this invention.

BACKGROUND OF THE INVENTION

1. Field of the Invention

The present invention relates to analyzing samples using evanescent wave biosensors. More specifically, the present invention relates to detecting single nucleotide polymorphisms in DNA samples using evanescent wave biosensors.

2. State of the Art

Over the past decade, molecular biology has been used to understand the molecular bases of inherited diseases. By identifying the gene or genes responsible for a disease, the genes of an afflicted person are compared to those of a non-afflicted person. In many diseases, the only difference between the genes of the afflicted and non-afflicted person is a single nucleotide polymorphism ("SNP") in the DNA sequence. Based on this SNP or mutation, it is sometimes possible to screen for the disease. Some diseases that have been investigated by molecular biologists include inherited cardiovascular diseases, such as arrhythmogenic right ventricular dysplasia, familial hypertrophic cardiomyopathy, idiopathic ventricular fibrillation, long-QT syndrome and Marfan Syndrome. Of these cardiovascular diseases, familial hypertrophic cardiomyopathy ("HCM"), long-QT syndrome ("LQTS"), and Marfan Syndrome ("MFS") are the best understood at the molecular level. Inheritance of these diseases is autosomal dominant and affected individuals are at risk of sudden cardiac death, often without previous symptoms. Since many of the genes responsible for these cardiac disorders, and a number of mutations in those genes, have been identified, it may be possible to use molecular diagnosis to screen individuals who may be at risk for sudden cardiac death.

Four genes have been implicated in LQTS, including KVLQT1, HERG, SCN5A, and KCNE1. Numerous mutations in these genes have been cataloged, including 75 mutations in KVLQT1, 84 mutations in HERG, 8 mutations in SCN5A, and 7 mutations in KCNE1. Of these four genes, the KVLQT1 gene is of great interest because it has been implicated in nearly 50% of the observed cases of LQTS in which the affected individual has been genotyped, a significant number of missense and deletion mutations have been identified in this gene by sequencing DNA from affected individuals, and the development of high-throughput screening assays for this gene may have a significant impact on treatment and patient outcomes. KVLQT1 encodes for a potassium channel in cardiac muscle, or at least the alpha subunit of the channel.

Numerous SNPs occurring in KVLQT1 have been associated with LQTS. The KVLQT1 gene comprises 16 exons that range in size from 47 base pairs for exon 14 to 386 base pairs for exon 1. A disproportionate number of these SNPs have been observed in exon 7, suggesting that exon 7 may be a mutational hot spot. However, SNPs have been observed in other exons. One polymorphism is G760A, which occurs in exon 3 of KVLQT1, in which guanine (G) at position 760 in the nucleotide sequence is replaced by adenine (A). This mutation results in the substitution of methionine for valine at position 254 in the amino acid sequence of the KVLQT1 protein.

Assessing polymorphisms in humans currently involves isolating the gene of interest from afflicted individuals using polymerase chain reaction ("PCR"), sequencing the genes, and then cataloging any observed polymorphisms or mutations. However, this procedure is too expensive and time-consuming to be used in routine patient screening. These disadvantages led to the development of DNA chips that contain hundreds or thousands of nucleic acid probe molecules immobilized to a single substrate in a two-dimensional array. These nucleic acid probes correspond to known mutations, such as missense mutations or deletions, which have already been cataloged. The nucleic acid probes are known as allele-specific oligonucleotides ("ASO"). However, patient screening with the DNA chip still involves isolating and amplifying the gene(s) of interest from the patient's DNA using PCR and then allowing the PCR product(s) to bind to the DNA chip. The chip is then washed and DNA hybridization is detected, usually by fluorescence, using either an epifluorescence or confocal microscope. This detection process is also time-consuming because each element in the ASO array is imaged sequentially for a few seconds or more. In other words, the detection is not in real-time. In addition, the instrumentation required to read the DNA chips is very expensive, costing between US $100,000 and US $200,000 for a typical setup.

While some polymorphisms include changes of multiple base pairs, other polymorphisms only include the change of a single base pair, known as an "SNP." For example, many of the mutations identified in the KVLQT1 gene are missense mutations involving a single, mismatched base pair. Traditionally, mismatched bases were distinguished by performing a hybridization reaction at a temperature below the melting temperature, $T_m$, of the homoduplex (hybrid of two wildtype oligonucleotides) but above the $T_m$ of the heteroduplex (hybrid of wildtype and mutant oligonucleotides). However, the melting temperature of a given DNA duplex varies with its content of A•T base pairs. Therefore, it is difficult to find a temperature that is optimal for the hundreds or thousands of oligonucleotides immobilized to the DNA chip.

One solution to this problem is to add either tetramethylammonium ("TMA") salts, such as TMA chloride, or betaine to the hybridization buffer. These compounds are thought to minimize the differences in melting temperature due to A•T content, thereby allowing all hybridization reactions to be performed at a single temperature that is optimal for distinguishing mismatched bases. However, high concentrations (1-2M) of these compounds are required, which makes them very viscous. This viscosity leads to manipulation problems and the high concentrations may interfere with enzymatic reactions. Another solution involves using modified nucleotides to either increase the stability of A•T base pairs or decrease that of G•C base pairs. Another variant of this approach is to add a few universal bases (5-nitroindoles) to the end of an A•T-rich oligonucleotide to increase its stability. Another solution is to allow the hybridization reaction to proceed to its maximum extent at a cold temperature (e.g., −20° C.) and then slowly ramp up the temperature of the DNA chip to 60° C. This allows an independent melting curve to be measured for every DNA duplex that has formed on the chip. While this approach is the most rigorous, it is also very slow and requires several hours to obtain a complete melting curve.

While hybridization techniques using ASO probes are used to screen for known mutations in the gene, an alternative technique is required to screen for mutations that have not been identified or cataloged. The current technique for detecting unknown mutations is fairly laborious and involves a technique called single-strand conformational polymorphism ("SSCP"). In this technique, PCR is used to amplify the region of interest, usually an exon. The PCR product is then denatured and run on an electrophoresis gel. In the single-stranded state, the nucleotide sequence of the PCR product affects its mobility, so an oligonucleotide containing a mutation migrates at a different rate on the gel than the wildtype sequence. The oligonucleotide containing the mutation is then isolated from the gel and sequenced to determine the position and composition of the mutation. However, the electrophoresis and sequencing steps are extremely time consuming.

An alternative for detecting unknown mutations in genes is sequencing by hybridization ("SBH"). In de novo SBH, a fragment of genomic DNA (usually 80-200 nucleotides in length) is exposed to a microarray of short oligonucleotides (usually 6 to 8 bases in length) that contain all possible sequence permutations. SBH has also been used to resequence a portion of the gene, of known sequence, that contains a genetic polymorphism in which a series of overlapping oligonucleotides is synthesized and immobilized on a microarray (or synthesized in situ on the chip). The sequence of each of these oligonucleotides is complementary to the gene of interest and is offset by one position relative to the preceding oligonucleotide in the series. Two strategies have been described for determining (or "calling") the sequence of the base(s) that have been changed by the mutation. In the first calling strategy, each position in the gene of interest is probed by four different oligonucleotides that are 25 bases in length, each of which is substituted with one of the four nucleotides in the middle ($13^{th}$) position.

The second calling strategy uses two types of oligonucleotide probes, a single series of overlapping capture oligonucleotides and a mixture of four different fluorescently-labeled sequencing oligonucleotides. Each of the fluorescently-labeled sequencing oligonucleotides contains a unique nucleotide at the 5' position but is degenerate at the other four positions. Resequencing is accomplished by first hybridizing oligonucleotides derived from the gene of interest to the microarray and then adding the mixture of fluorescently-labeled sequencing oligonucleotides. The fluorescently-labeled sequencing oligonucleotides are typically too short to hybridize on their own, but may hybridize in a tandem fashion immediately adjacent to one of the capture oligonucleotides, forming a stable, but nicked, DNA duplex. Even though this nicked duplex has been shown to be thermodynamically stable, the capture and fluorescently-labeled sequencing oligonucleotides may also be ligated using polynucleotide ligase for improved stability.

Optical sensors, such as evanescent wave biosensors, are commonly used to detect various substances, or analytes, in diagnostic and research settings. For example, the BIACORE® biosensor, available from Biacore AB (Uppsala, Sweden), is based on surface plasmon resonance ("SPR") and is used to monitor biomolecular interactions in real-time without the use of fluorescent or radio labels. Affinity Sensors (Cambridge, England), a division of Thermo BioAnalysis Corp., makes a similar system called IAsys® that uses a slightly different optical geometry referred to as "resonant mirrors." Both of these systems respond to changes in an index of refraction in an evanescent wave. The changes occur when a ligand, with a refractive index greater than that of water, binds to an immobilized capture molecule on the surface of the sensor. Examples of such binding include soluble antigens binding to immobilized antibodies and single-stranded PCR products binding to immobilized oligonucleotides. The devices produced by Biacore AB and Affinity Sensors are mass sensors because the signals change in proportion to the mass bound within the evanescent field. Both Biacore AB and Affinity Sensors have modeled the kinetics of mass binding to the sensor and have determined the relationship between ligand concentration in bulk solution and binding rate.

Surface plasmon resonance and resonant mirror sensors represent a specialized application of a more general surface sensitive optical technique called attenuated total reflection ("ATR") that preferentially interrogates sample bound to the solid/liquid interface via the evanescent wave. In most ATR geometries, the interrogating radiation is confined to a thick waveguide in which light propagates in a simple zig-zag pattern. To a first approximation, the interaction of the evanescent wave with a surface bound sample increases linearly with the number of reflections per centimeter (N) of the light at the waveguide-solution interface. This number may be calculated using the simple expression $N = \cot \theta / 2D$, where D and $\theta$ are the waveguide thickness and mode propagation angle, respectively (Figure B.1). Thus, for a given surface optical measurement at a specified angle of reflection, a 1 µm thick glass waveguide may be 150 times more sensitive than a 150 µm thick glass coverslip, and 1000 times more sensitive than 1 mm thick glass microscope slide.

Evanescent wave biosensors also include fiber and planar waveguides, which are so thin that incoupled light no longer propagates as a simple ray of light. Instead, when the waveguide thickness is on the order of microns, the incoupled light forms constructive and destructive interference patterns. Guided modes are a discrete set of constructive interference patterns that allow light to propagate down the waveguide. In general, greater than 95% of the guided light is confined to the waveguide itself. The evanescent wave refers to the remaining 5%, or less, of light intensity that penetrates just a few tenths of a micron into the lower refractive index media adjacent to the waveguide surface.

Planar waveguides are known in the art and are of a generally planar shape comprising two planar surfaces spaced by a width. Different types of planar waveguide sensors are known in the art, including injection-molded thick-film waveguides and integrated optical thin-film waveguides ("IOW"). Planar waveguides are described in U.S. Pat. Nos. 5,512,495, 5,677,196, 5,846,842, and 6,222,619 (all issued to Herron et al.) and U.S. Pat. Nos. 5,832,165, 5,814,565 (all issued to Reichert et al.), the disclosures of which are hereby incorporated herein, in their entireties, by this reference.

Evanescent wave biosensors are designed to function with or without fluorescent labels. As mentioned previously, surface plasmon resonance and other label-free optical sensors respond to mass changes in the evanescent wave. However, mass sensors have at least two limitations over fluorescent sensors. First, a mass sensor responds to any molecule bound within the evanescent wave, whether it is bound specifically or non-specifically. For this reason, nonspecific binding ("NSB") is a significant problem with mass sensors. Both Biacore AB and Affinity Sensors have devoted significant efforts to developing immobilization chemistries with low NSB. The second limitation is that mass sensors require a significantly larger sensing area to measure a given concentration of analyte than a fluorescent sensor because mass detection is less sensitive than fluorescent detection. Therefore, to detect low levels of an analyte, the sensitivity of fluorescence detection is preferred.

In contrast, detection in a fluorescent biosensor is accomplished by the specific binding of a fluorescently-labeled "tracer" molecule to the ligand-capture molecule complex. The specific binding is accomplished through an affinity interaction, including, but not limited to, the binding of soluble antigens to immobilized antibodies or single-stranded PCR products to immobilized oligonucleotide probes. Alternatively, a fluorescently-labeled analyte or ligand molecule binds directly to the immobilized capture molecule. This latter situation is preferable for nucleic acid hybridization assays because the fluorescent label is directly incorporated into the analyte molecule using PCR. In either of these cases, NSB is only an issue with the fluorescently-labeled molecule, rather than with any molecule that happens to be in the evanescent wave. Therefore, fluorescence is a preferable method of detection.

More specifically, optical biosensors are used to perform nucleic acid probe assays, also known as molecular diagnostics or MDx assays. It is known that the hybridization kinetics of heteroduplex DNA is slower and reach a lower steady-state value than that of homoduplex DNA. In addition, variability in the A•T content and oligonucleotide length affect the hybridization kinetics. It is possible to control for these factors by using pairs of wildtype and mutant probes and taking the ratio of the two hybridization rates ($R_{mut}/R_{wt}$), thereby normalizing for A•T content and oligonucleotide length.

While a majority of the biosensors known in the art are fluorescent fiber optic sensors or label-free surface plasmon resonance sensors, other label-free evanescent wave formats have been described including interferometry, diffractometry and evanescent-illuminated light scatter. Recently, the use of evanescent wave biosensors in clinical applications has been disclosed. In Nilsson et al. (Nilsson, P., B. Persson, A. Larsson, M. Uhlen and P. A. Nygren "Detection of mutations in PCR products from clinical samples by surface plasmon resonance" *J Mol Recognit* 10, 7-17 (1997)), surface plasmon resonance is used to detect the presence of the human tumor suppressor p53 gene in breast tumor biopsy material. SNPs in clinical DNA samples are detected by comparing the rate of hybridization of PCR products to the rate of hybridization of the wildtype. The PCR products, which contained mismatched bases, give reduced levels of hybridization relative to the wildtype.

In Pilevar et al. (Pilevar, S., C. C. Davis and F. Portugal "Tapered optical fiber sensor using near-infrared fluorophores to assay hybridization" *Anal Chem* 70, 2031-7 (1998)), 25 pM levels of *Helicobater pylori* RNA are detected using a fluorescent fiber optic sensor, showing that fluorescent evanescent wave sensors are capable of performing highly sensitive MDx assays.

Schneider et al., *Clinical Chemistry*, 43(9):1757-1763 (1997) discloses using a Hartman interferometer to detect real-time hybridization of nucleic acids. The Hartman interferometer is an optic sensor that uses a single planar wave of linearly polarized light to detect the hybridization of target nucleic acids to a complementary single-stranded probe. The assay is able to differentiate between sequences with a 4-base pair mismatch.

In Stimpson et al., *Genetic Analysis: Biomolecular Engineering*, 13:73-80 (1996), an optical waveguide is used to detect SNPs by monitoring the binding and dissociation kinetics of oligonucleotide complexes to oligonucleotide probes. The SNPs are detected by a signal produced by a selenium conjugate.

Jensen et al., *Biochemistry*, 36:5072-5077 (1997) discloses using hybridization kinetics to detect SNPs between nucleic acid mimics, such as peptide nucleic acid ("PNA")-DNA and PNA-RNA duplexes. The SNPs are detected using surface plasmon resonance.

In Bianchi et al., *Clinical and Diagnostic Virology*, 8:199-208 (1997), surface plasmon resonance is used in a nucleic acid hybridization assay to detect mutations in HIV-1 genomic sequences. The assay uses hybridization kinetics and real-time monitoring to detect the mutations.

Abel et al., *Anal. Chem.* 68:2905-2912 (1996) discloses using nucleotide hybridization assays to detect small variations in nucleic acid sequences. The variations are detected by fluorescence using a fiber optic sensor.

Publication WO 99/47705 discloses using a planar waveguide in a nucleic acid hybridization assay to detect a target polynucleotide. The assay uses fluorescence to detect hybridization.

Publications WO 96/35940, WO 95/33197, and WO 95/33198 disclose assays that use at least one planar waveguide to quantitatively detect an analyte of interest in an opaque fluid. The assays use fluorescent dyes to determine nucleic acid hybridization and acquire data in real-time.

Thus, a need remains for an improved method of detecting SNPs using an evanescent wave sensor. A need further remains for a method of detecting SNPs that uses a planar waveguide in a fluorescence assay. The method may reduce assay time by monitoring fluorescence in real-time. A need also remains for a high-throughput genetic screening assay for detecting known and unknown mutations in a gene of interest.

SUMMARY OF THE INVENTION

The present invention relates to a method of detecting an SNP in a gene of interest. A plurality of wildtype and SNP probes are immobilized on a planar waveguide. A fluorescently labeled analyte is then flowed over the planar waveguide. Binding of the analyte to the wildtype and SNP probes is detected in real-time and the hybridization kinetics are compared. The wildtype probe comprises a nucleotide sequence complementary to a wildtype sequence of the gene of interest, while the SNP probe comprises a nucleotide sequence complementary to a sequence containing an SNP of the wildtype sequence.

The present invention also discloses a method of detecting SNPs in a gene of interest by sequencing by hybridization.

DETAILED DESCRIPTION

Figure 1:
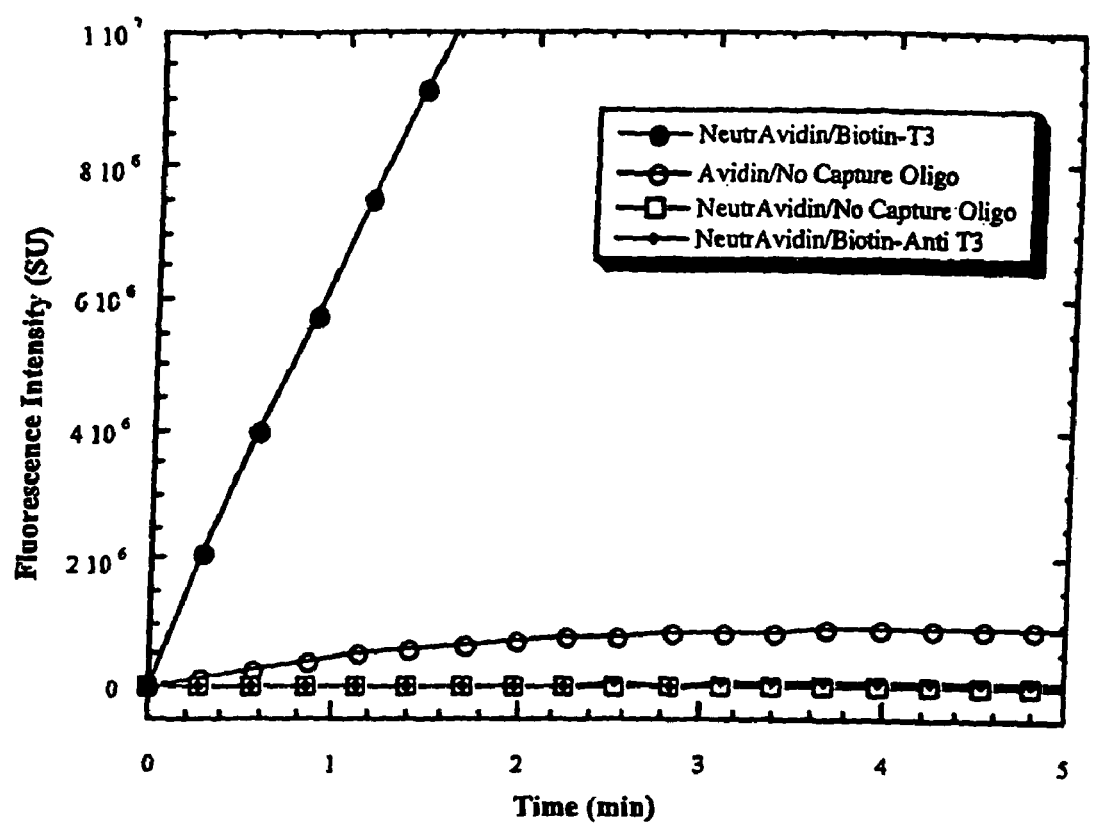
FIG. 1 shows the binding of Cy5-labeled anti T3 to several different capture probes. Open circles: nonspecific binding to immobilized avidin. Open squares: nonspecific binding to neutravidin. Closed diamonds: nonspecific binding to immobilized biotin-anti T3/neutravidin complex. Closed circles: hybridization to immobilized biotin-T3/neutravidin complex.

The present invention relates to detecting SNPs in a gene of interest in fluorescently labeled DNA samples. Planar waveguide fluorescent biosensor technology is used to detect the SNPs using a nucleic acid hybridization assay, wherein a plurality of SNP probes and wildtype probes are immobilized on the waveguide. The SNP is detected by monitoring in real-time the hybridization kinetics of the DNA sample binding to the SNP and wildtype probes.

The present invention also relates to detecting SNPs in synthetic oligonucleotide samples using evanescent wave biosensors. A capture probe comprising a nucleotide sequence complementary to a gene of interest is immobilized on a planar waveguide. Two analytes are synthesized and fluorescently labeled. A wildtype analyte comprises a nucleotide sequence complementary to the sequence of the capture probe. An SNP analyte comprises a sequence with an SNP in comparison to the sequence of the wildtype analyte. The SNP is detected by monitoring, in real-time, the hybridization kinetics of the analytes binding to the capture probe.

A method of detecting SNPs by SBH is also disclosed. A capture probe is immobilized on the planar waveguide and four different fluorescently-labeled degenerate sequencing probes (AXXXX-Cy5, CXXXX-Cy5, GXXXX-Cy5, and TXXXX-Cy5) (SEQ ID NOS: 16, 13, 15, and 14, respectively)are synthesized. Resequencing is accomplished by hybridizing analyte probes derived from the gene of interest to the capture probe. Then, the sequencing probes are added. Each of the combinations of analyte probe, capture probe, and sequencing probe gives a different hybridization rate. The analyte probe that has the middle mutant nucleotide matching the nucleotide in the sequencing probe has the highest hybridization rate while mismatched pairs show lower rates (rejections). Four different fluorescently labeled nondegenerate sequencing probes may also be synthesized and used for resequencing.

In one embodiment, a plurality of SNP probes may be immobilized on a planar waveguide. A plurality of wildtype probes, each of which comprises a sequence complementary to a wildtype sequence of a gene of interest, may also be immobilized on the planar waveguide. The sequences of the wildtype and SNP probes may differ by a single base. A solution comprising a fluorescently-labeled analyte may then be flowed or passed over the planar waveguide. The binding between the analyte and each of the wildtype and SNP probes may cause a detectable change in the fluorescence signal. The amount of fluorescence may depend on the level of binding between the analyte and the SNP probe and the analyte and the wildtype probe. The presence of the SNP in the analyte may be detected by comparing the hybridization kinetics of the analyte with the SNP probe and the hybridization kinetics of the analyte with the wildtype probe.

The analyte may comprise a DNA sample, such as a single-stranded PCR product or DNA isolated from a patient. The analyte may be a gene of interest, or a region thereof, isolated from the patient. During optimization of the assay, it is also contemplated that two analytes may be used. These two analytes may be synthetic oligonucleotides that resemble single-stranded oligonucleotides isolated and amplified from patient DNA. One of the analytes, a wildtype analyte, is complementary to the wildtype probe, while the second analyte, an SNP analyte, is complementary to the SNP probe.

The analyte may be labeled with a fluorescent dye that is stimulated to fluoresce by the wavelength of light emitted by a light source. For example, if the light source emits red light, the analyte may be labeled at its 5' end with a fluorescent dye that may be excited, or stimulated, by excitation with wavelengths in the red spectral region. Such a dye is Cy5, a red-emitting fluorescent dye available from Biological Detection Systems, Inc., of Pittsburgh, Pa., or Amersham Biosciences Corp. of Piscataway, N.J. However, it is also contemplated that other dyes that may be excited, or stimulated, into fluorescence with wavelengths in the red spectral region may be used. The analytes may be prepared by PCR and Cy5-labeled primers may be used to initiate DNA synthesis. Thus, the PCR product may contain Cy5 dye at its 5' end.

The SNP probe may comprise a nucleotide sequence that is complementary (in a binding sense) to a sequence of a known SNP in the gene of interest. In other words, the SNP probe may be complementary to a sequence containing an SNP of the wildtype sequence. The SNP and wildtype probes may be immobilized on the planar waveguide by means known in the art. Preferably, the SNP and wildtype probes are immobilized on the waveguide using a protein-resistant coating, such as avidin or neutravidin. The SNP and wildtype probes are also known as allele-specific oligonucleotide ("ASO") probes. The SNP and wildtype probes may be 15-25 nucleotides in length, with the mutation site located near the middle of the sequence.

In another embodiment, it is contemplated that one probe, a capture probe, may be immobilized on the planar waveguide. The capture probe may comprise a nucleotide sequence complementary to the gene of interest, or region thereof. Two analytes are synthesized, a wildtype analyte and an SNP analyte, rather than obtaining DNA or PCR products from a patient. The wildtype analyte comprises a nucleotide sequence complementary to the sequence of the capture probe. The SNP analyte comprises a sequence almost identical to that of the wildtype analyte, except for a single, mismatched pair at one position.

The planar waveguides of the present invention may comprise injection-molded thick-film waveguides or IOWs. The substrate of the planar waveguide may be a square or rectangular glass microscope slide or coverslip. Other materials for the substrate may include, but are not limited to, high-lead glass, quartz, or optical plastic. Injection-molded thick-film waveguides are available from Opkor, Inc., of Rochester, N.Y. Since these waveguides are disposable and relatively inexpensive, they may be preferred in assay development for known and unknown mutations in a gene of interest. IOWs used in the present invention are based on a patented design and are available from Dr. Reichert at Duke University, in Durham, N.C. IOWs may be used when hundreds or thousands of oligonucleotide hybridization assays per sensor are required.

To provide the high-throughput screening feature of the present invention, the density of hybridization probes immobilized on the planar waveguide may be dramatically increased. To increase the density, the probes may be patterned onto the planar waveguides by various techniques. Several patterning methods are known for immobilizing microarrays of hybridization probes to solid surfaces, including printing, stamping and photopatterning. In printing, hybridization probes may be sprayed onto the surface of the planar waveguide using an ink jet printer. In stamping, the hybridization probes may be spotted onto the surface of the planar waveguide using an array of pins or micropipettes. Printing and stamping may allow 100-200 array elements to be patterned on a single planar waveguide. For patterning 1000+ array elements, photopatterning or photolithography may be used.

The planar waveguides are used in conjunction with a flowcell developed by Drs. Herron, Christensen and Reichert. The flowcells are constructed from two separate pieces, a top and a bottom plate, that are fabricated from aluminum. The top plate is milled to produce one, two or three parallel flow chambers, each with small inlet and outlet ports. The interior of the bottom plate is milled to support the waveguide and provide a clear view of its bottom. The entire flowcell is anodized to be flat black. The top plate is sealed against the waveguide using a composite gasket with a low-refractive index Teflon™ layer next to the waveguide and a silicon rubber layer next to the top plate. Mechanical pressure to seal the system is produced by tightening four knurled bolts located at the four corners of the flowcell.

A computer-controlled 3-barrel syringe pump, available from Tecan Systems, Inc., of San Jose, Calif. (formerly Cavro Scientific Instruments, Inc.), is used to inject specimens into the flow chambers. The sample volume of each chamber is 100 µL. The temperature of the flowcell is controlled by a computer-controlled Peltier device that is mounted on the top plate of the flowcell. The temperature is varied over a range of $-10°$ C. to $80°$ C. Both the syringe pump and the Peltier device are controlled by an instrument control and data acquisition program that was written in the LabView macro language. This software runs on either MacOS or Windows platforms.

The availability of different top plates (1-, 2- or 3-chamber) affords flexibility in experimental design. For example, the PCR product generated from a nucleic acid sample obtained from a single patient may be screened for a large number of mutations in the gene of interest using a single chamber flowcell, or PCR products obtained from three different patients may be screened for a smaller number of mutations using a 3-chamber flowcell. Alternatively, the extra chambers may be used for calibration purposes. For instance, the PCR product is injected into one chamber, while positive and negative controls are injected into the other two chambers.

Any means of detecting the change in fluorescence caused by the hybridization of the analyte to the SNP or wildtype probes may be used. The detector may comprise a photodetector useful in detecting light in the wavelength region of the emitted fluorescence, as known in the art. Preferably, the change in fluorescence is monitored in real-time using a charge coupled device ("CCD") camera or a complementary metal-oxide-semiconductor ("CMOS") imager of a known type.

The hybridization kinetics may be examined under various experimental conditions by optimizing factors such as the oligonucleotide length, assay temperature, and hybridization buffer. Under normal conditions, the analyte may hybridize with both the SNP and wildtype probes, with different reaction kinetics and equilibrium duplex concentrations. As previously discussed, it is known that the hybridization kinetics of heteroduplex (hybrid of wildtype and mutant oligonucleotides) DNA is slower than that of homoduplex (hybrid of two wildtype oligonucleotides) DNA. Therefore, the hybridization rate of the analyte to the SNP probe is lower than the hybridization rate of the analyte to the wildtype probe. Since the sequences of the two probes differ by one base pair, the SNP may be detected by comparing the hybridization rates.

Since the wildtype and SNP probes differ by only one base, a significant level of hybridization is expected between the analyte with both probes, especially at temperatures well below their denaturization, or melting, temperatures. To further increase differences between the hybridization kinetics, or differentiate the hybridization kinetics, hybridization conditions such as temperature, pH, and counter ion concentrations may be altered. The desired differentiation in hybridization rate may by achieved by adding TMA salts or betaine to the hybridization buffer. In addition, modified nucleotides may be used to increase the stability of A•T base pairs. It is also known that hybrids of PNA and DNA may be more stable than DNA/DNA duplexes and that mismatched bases have a greater destabilizing effect on the melting temperature of PNA/DNA hybrids than on duplex DNA. Therefore, it is also contemplated that the hybridization probes of the present invention may be replaced with their PNA equivalents.

The hybridization kinetics may also be used as a means for optimizing assay temperature and hybridization probe length. During assay optimization, a pair of fluorescently-labeled model analytes may be used in lieu of PCR-amplified patient DNA. Two different analytes may be required for each mutation. For example, one analyte, the wildtype analyte, contains the wildtype sequence while the second analyte, the SNP analyte, contains the SNP. The model analytes may be synthetic oligonucleotides that resemble singled-stranded oligonucleotide sequences isolated and amplified from patient DNA using PCR. The model analytes may be labeled at the 5' end with Cy5 and may be analogous to PCR products that were produced using initiation primers labeled at the 5' end with fluorescent dyes. Once assay conditions and waveguide patterning procedures have been optimized, the multi-channel nature of the planar waveguide technology may allow hundreds of probes to be immobilized on one planar waveguide.

Fluorescence measurements are taken with a Mark 1.5 evanescent wave imaging fluorometer that was constructed by Dr. Douglas Christensen at the University of Utah. Planar waveguides are mounted in the flowcell to form the sensor assembly, as described above. The sensor assembly is then locked into a mounting plate on the Mark 1.5 fluorometer that provides tight registration of the waveguide to the exciting light. A diode laser that emits 12 mW of red light at 635 nm is used as the light source. The output of this laser is formed into a sheet beam using a series of collimating lenses and then reflected with a mirror into the IOW's diffraction grating (or coupling lens in the case of thick-film waveguides). Once trapped inside the planar waveguide, the light bounces from side to side of the waveguide setting up an evanescent field at each reflection point.

This evanescent field decays about 100 nm into the solution in the flowcell and excites Cy5-labeled analytes that are hybridized to the capture probes. Fluorescence emission emanates in all directions. The portion of the fluorescence emission that travels through the planar waveguide, and through a window in the bottom of the flowcell, is collected and imaged by the CCD camera (Santa Barbara Instrument Group). This camera is equipped with a 55 mm f/2.8 macro lens (Nikon) to focus the light, and a 670 nm bandpass interference filter (Orion) to reject scattered light. The CCD image is collected and processed by the aforementioned instrument control and data acquisition program that is written in the LabView macro language. This software "bins" the image into different spatially-resolved sensor zones and also uses a non-linear least squares fitting routine to compute the average hybridization rate of a data set over a 5 min. assay period.

In yet another embodiment, SNPs in the KVLQT1 gene may be detected. As previously discussed, many of the mutations in KVLQT1 are SNPs. Since the presence of the SNP alters the hybridization of two nucleotide sequences, the SNP in the KVLQT1 gene may be detected by monitoring the hybridization kinetics, as described above. To detect SNPs in KVLQT1, a pair of capture probes may be synthesized for each of the known SNPs in KVLQT1. One of the capture probes may be the SNP probe and may comprise a nucleotide sequence complementary to the sequence of the known SNP in KVLQT1. The second probe may be the wildtype probe and comprise a sequence complementary to KVLQT1, or a region thereof. Preferably, the sequences of the two probes differ by one nucleotide. Each of the probes may be biotinylated at the 5' end and immobilized to a neutravidin-coated planar waveguide. A solution comprising a DNA sample obtained from a patient may then be passed over the planar waveguide to determine whether the DNA sample has the known SNP. Since LQTS is autosomal-dominant, most affected individuals are heterozygous for the mutation and may have one wildtype and one mutant allele. Individuals who are homozygous for the wildtype sequence may have a low hybridization ratio, approaching zero, while heterozygous individuals may have a ratio approaching unity. The rare individuals who are homozygous for the mutation may have a ratio significantly greater than one.

While the allele-specific hybridization approach described above may be used to screen patients for known mutations in the KVLQT1 gene, SBH may be required to identify mutations in KVLQT1 that have not previously been cataloged. SBH may be compatible with the IOW sensor format, although a complete implementation for the KVLQT1 gene may require an array of about 2000 decanucleotide (10-mers) hybridization probes to be immobilized to the waveguide. While that number of hybridization probes is within the capabilities of the IOW sensors, it may be too large for a feasibility study.

To determine whether SHB may be successful in a high-throughput screening assay, short sequences (5-10 nucleotides in length, preferably 4-8 nucleotides in length) that contain a single point mutation may be screened. In addition, a series of model analytes that include the wildtype sequence and all possible mutations at each of the positions being resequenced may be synthesized. The planar waveguide biosensor may be used to monitor the hybridization rate for resequencing the portion of interest of the gene of interest that contains a single polymorphism. A 10-mer capture probe may be immobilized on the planar waveguide and four different fluorescently-labeled degenerate sequencing probes (AXXXX-Cy5, CXXXX-Cy5, GXXXX-Cy5, and TXXXX-Cy5) (SEQ ID NOS: 16, 13, 15, and 14, respectively)) may be synthesized. Resequencing may be accomplished by first hybridizing analyte probes (e.g., 21-mers), which are derived from the gene of interest, to the capture probe on the waveguide surface. Then, the sequencing probes may be added. Each of the analyte probes, which are substituted with one of the four nucleotides in the middle (e.g., $11^{th}$) position, may give a different hybridization rate. The analyte probe that has the middle mutant nucleotide matching the nucleotide in the sequencing probe, may give the highest hybridization rate while mismatched pairs may show lower rates (rejections). Four different fluorescently labeled nondegenerate sequencing probes may also be synthesized and used for resequencing.

Since the success of SBH depends on how well the hybridization rates for homoduplex and heteroduplex formation are differentiated, the desired differentiation may require adding TMA salts or betaine to the hybridization buffer, modifying the nucleotides, or using PNA probes, as previously discussed.

If SBH is successful on these short sequences, larger regions of the gene, such as a single transcribed region (exon), from the KVLQT1 gene may be resequenced before the entire KVLQT1 gene is resequenced. Since the nucleotide primers used for isolating the KVLQT1 gene (and other LQTS genes) from patient DNA are organized at the exon level, resequencing arrays may be made that correspond to the different exons within KVLQT1. Therefore, resequencing any of these exons may be accomplished with a medium-density array of capture probes.

As previously mentioned, a large number of SNPs have been mapped to exon 7 of KVLQT1 and exon 7 may be a mutational hot spot. Therefore, exon 7 may be a good candidate to determine the viability of SBH. Since exon 7 is only 111 base pairs in length, it may require a resequencing array of approximately 400 oligonucleotides using the first calling method, but only about 100 oligonucleotides using the second calling method. However, it is also contemplated that SNPs in other exons may be used.

Resequencing of the entire gene may be accomplished by first hybridizing the oligonucleotides, which may be 80-200 nucleotides in length and are derived from the KVLQT1 gene, to the microarray and then adding the mixture of sequencing probes. The sequencing probes (5-mers) are too short to hybridize on their own accord but may hybridize in a tandom fashion immediately adjacent to one of the capture probes (10-mers), forming a stable, but nicked, DNA duplex that is 15 nucleotides in length. Even though this nicked DNA duplex has been shown to be thermodynamically stable, the capture and sequencing probes may also be ligated using polynucleotide ligase for improved stability. Since the redundancy in this strategy resides in the sequencing rather than in the capture probes, a full genetic screen of KVLQT1 may require about 2000 capture probes.

In addition to detecting SNPs in KVLTQ1, these techniques may be adapted to detect SNPs in the three, remaining genes (HERG, SCN5A, and KCNE1) that have been implicated in LQTS. In addition, the techniques may be used to simultaneously screen for SNPs in all four genes. Furthermore, while detecting SNPs in genes implicated in inherited cardiovascular diseases has been described, this technology may be adapted to detect SNPs in the genes implicated in any disease. Therefore, this technique is well-suited for almost any high-throughput screening application in molecular diagnostics.

The invention is further explained by the following illustrative examples.

EXAMPLES

Example 1

To monitor the hybridization of two complementary oligonucleotides in real-time, the T3 RNA polymerase promoter site was chosen as a model system. The T3 site is a region spanning 20 bases with the following sequence: 5' AATTAACCCTCACTAAAGGG 3' (SEQ ID NO:1). Oligonucleotide primers for both the T3 sequence and its complementary sequence, anti T3, are commercially available. They have also been fluorescently labeled and used in nucleic acid sequencing.

An avidin/biotin system was used for immobilizing the T3 oligonucleotide to the waveguide based on previous observations that avidin adsorbed equally well to both integrated optical waveguides and injection-molded waveguides. The T3 20-mer was biotinylated at the 5' end via a six-carbon spacer and was then immobilized to planar waveguides, either injection-molded or integrated optical, that had been previously coated with either avidin or neutravidin. The anti T3 20-mer was labeled at the 5' end with Cy5, a red-emitting fluorescent dye. The resulting Cy5-labeled analyte was very similar to analytes that may be used in clinical MDx assays.

The kinetic response of the injection-molded biosensor for the T3/anti T3 hybridization reaction is shown in FIG. 1, along with three controls. A solution of 10 nM Cy5-labeled anti T3 was injected into the flowcell in all four cases, but a different capture molecule, or complex, was examined in each case. Nonspecific binding of Cy5-anti T3 to either avidin or neutravidin is depicted in open circles and open squares, respectively. Interestingly, a significant level of NSB was observed with avidin, but not with neutravidin. Presumably, this is because avidin has a high pI value and is positively-charged at pH 7.4, which may lead to electrostatic interactions with the negatively-charged tracer oligonucleotide. Based on this observation, neutravidin was used instead of avidin in subsequent studies. The third control examined whether there was any nonspecific binding between two oligonucleotides with the same nucleotide sequence. In this case, biotinylated anti T3 was immobilized to a neutravidin-coated waveguide (closed diamonds). Binding between like oligonucleotides was negligible. Finally, hybridization between complementary oligonucleotides was examined by immobilizing biotinylated T3 to a neutravidin-coated waveguide (closed circles). Very strong binding was observed, reaching $10^7$ sensor units in less than two minutes. Similar results were also obtained using IOWs as the planar waveguides (data not shown).

Example 2

Figure 2:
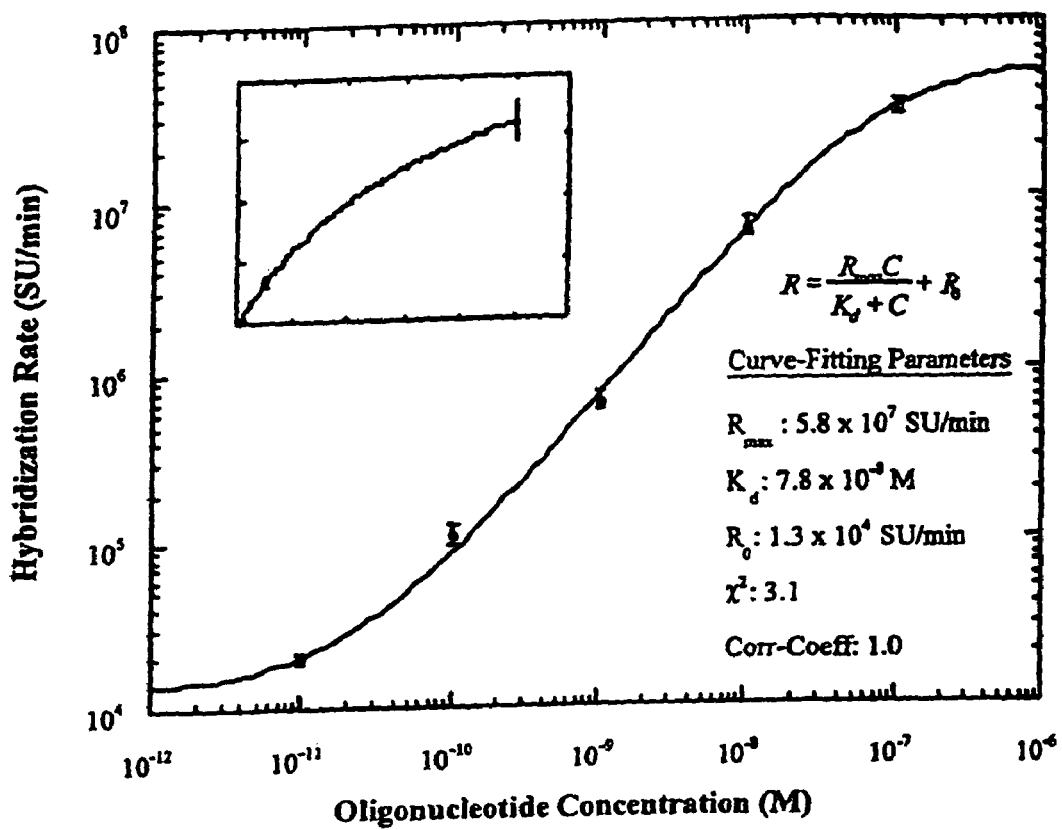
FIG. 2 is a standard curve for the hybridization of Cy5-anti T3 to immobilized T3. The sensitivity of the T3/anti T3 hybridization assay using injection-molded, thick-film waveguides was investigated by spiking human Cy5-labeled anti-T3 into PBS. Binding rate was plotted versus Cy5-anti T3 concentration to construct the standard curve. An analytical sensitivity (defined as 2σ/slope, where σ is the standard deviation of the zero rate) value of 1.4 pM was determined for the assay.

T3/anti T3 hybridization assays were performed at room temperature for numerous concentrations of Cy5-labeled anti T3, ranging from 10 pM to 100 nM. The binding rate was plotted versus tracer oligonucleotide concentration in FIG. 2. A double log plot was used due to the wide dynamic range (4 orders of magnitude) of the assay. The same data is plotted on linear axes in the inset. The data was found to fit a Michaelis-Menton model with a Michaelis constant of about 78 nM (curve-fitting parameters are also shown in the figure). An analytical sensitivity value of 1.4 pM was computed for these data. These results showed that the biosensor is an ideal platform for performing MDx assays because it is both sensitive (low picomolar levels) and rapid (5 minute assays) and offers the additional advantage of being able to monitor hybridization reactions in real-time.

Example 3

To determine whether mismatched bases cause a change in the oligonucleotide hybridization kinetics, a prostate specific antigen ("PSA") model system was used. PSA exhibits a high degree of homology to the human protein glandular kallikrein (hGK2), which is also secreted by the prostate gland. Therefore, in hybridization studies, it is important that the immobilized hybridization probe bind only to cDNA derived from the PSA message, and not to that derived from the hGK2 message. A region in exon 4 of the PSA gene comprises a sequence that differs from hGK2 in 7 out of 20 positions. A hybridization probe (5'-GGGGC AAAAGCACCTGCTCG-3') (SEQ ID NO:2), referred to as anti PSA, that recognizes this sequence was synthesized and biotinylated at the 5' end. Two additional oligonucleotides were synthesized, labeled with Cy5, and used as model analytes. One of these oligonucleotides (5'-CGAGCAGGTGCTTT TGCCCC-3') (SEQ ID NO:3), referred to as PSA, was derived from the cDNA sequence of PSA. The other oligonucleotide (5'-CCA•CAA GTGTCTTTACCAC-3') (SEQ ID NO:4), referred to as hGK2, was derived from the cDNA sequence of hGK2.

Figure 3:
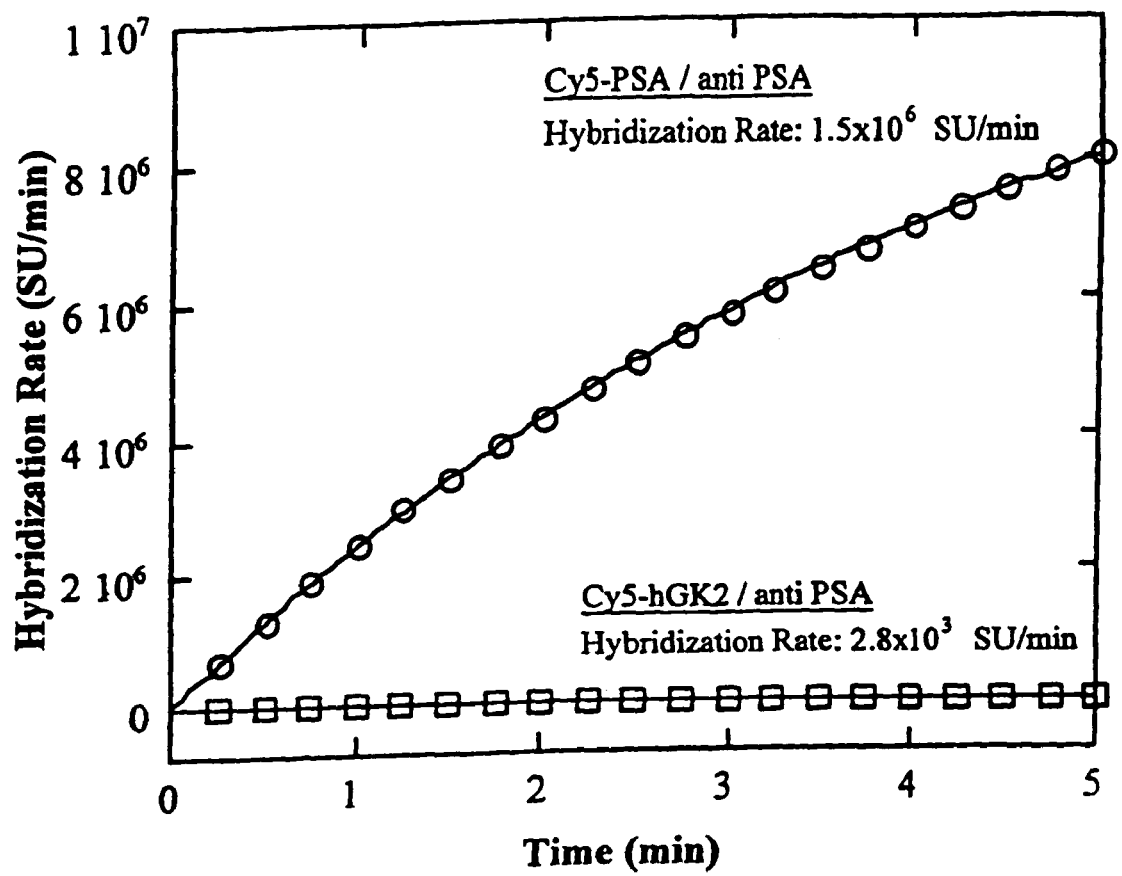
FIG. 3 shows the hybridization kinetics of two Cy5-labeled oligonucleotides (PSA & hGK2) to an immobilized oligonucleotide (anti PSA). PSA and anti PSA are perfectly complementary and exhibited a high hybridization rate (1.5× $10^6$ sensor units per minute). The hGK2 and anti PSA oligonucleotides have mismatched bases in 7 out of 20 positions and exhibited a much lower hybridization rate (2800 SU/min.)

The biotinylated anti-PSA probe was immobilized to a neutravidin-coated, injection-molded waveguide. A 1 nM solution of either Cy5-labeled PSA or Cy5-labeled hGK2 was injected into the flowcell. Hybridization kinetics curves are shown in FIG. 3 for both of these reactions. A very high hybridization rate was observed for the homoduplex (shown as open circles), while the rate observed for the heteroduplex (shown as open squares) was not statistically above background. With this much difference in hybridization rate with seven mismatched bases, a significant difference may be observed for a single mutation.

Example 4

The G760A polymorphism occurs in exon 3 of the KVLQT1 gene. A 5'-biotinylated capture probe was synthesized for detecting this polymorphism. The capture probe was 21 nucleotides in length and complementary to positions nos. 750-770 of the KVLQT1 gene. The sequence of the capture probe is given below:

```
Capture probe:
  5'-biotin-ATGAAGACCACGGAGCCCAGG-3'     SEQ ID NO:5
```

During assay development and feasibility testing, synthetic oligonucleotides were used as analytes rather than PCR products derived from human sources. The analyte were 21 nucleotides in length and 5'-labeled with Cy5, obtained from Amersham Biotechnology. The sequences of the analytes corresponded to positions 750-770 of the KVLQT1 gene, except for position 760 (position 11 in the synthetic analytes), which contained either a G (wildtype analyte) or A (G760A polymorphic analyte). The sequences of the wildtype and SNP analytes are given below:

```
Wildtype analyte:
  5'-Cy5-CCTGGGCTCCGTGGTCTTCAT          SEQ ID NO:6

G760A analyte:
  5'-Cy5-CCTGGGCTCCATGGTCTTCAT          SEQ ID NO:7
```

Both of the analytes were synthesized by a peptide and nucleic acid synthesis facility at the University of Utah. All products were then purified using high performance liquid chromatography ("HPLC") to remove excess salts and the "n−1" oligonucleotides that had a base deletion. A mass spectrum was then performed on each of the products to verify purity. Products with poor mass spectra were resynthesized, purified, and run until all products were pure.

Figure 4:
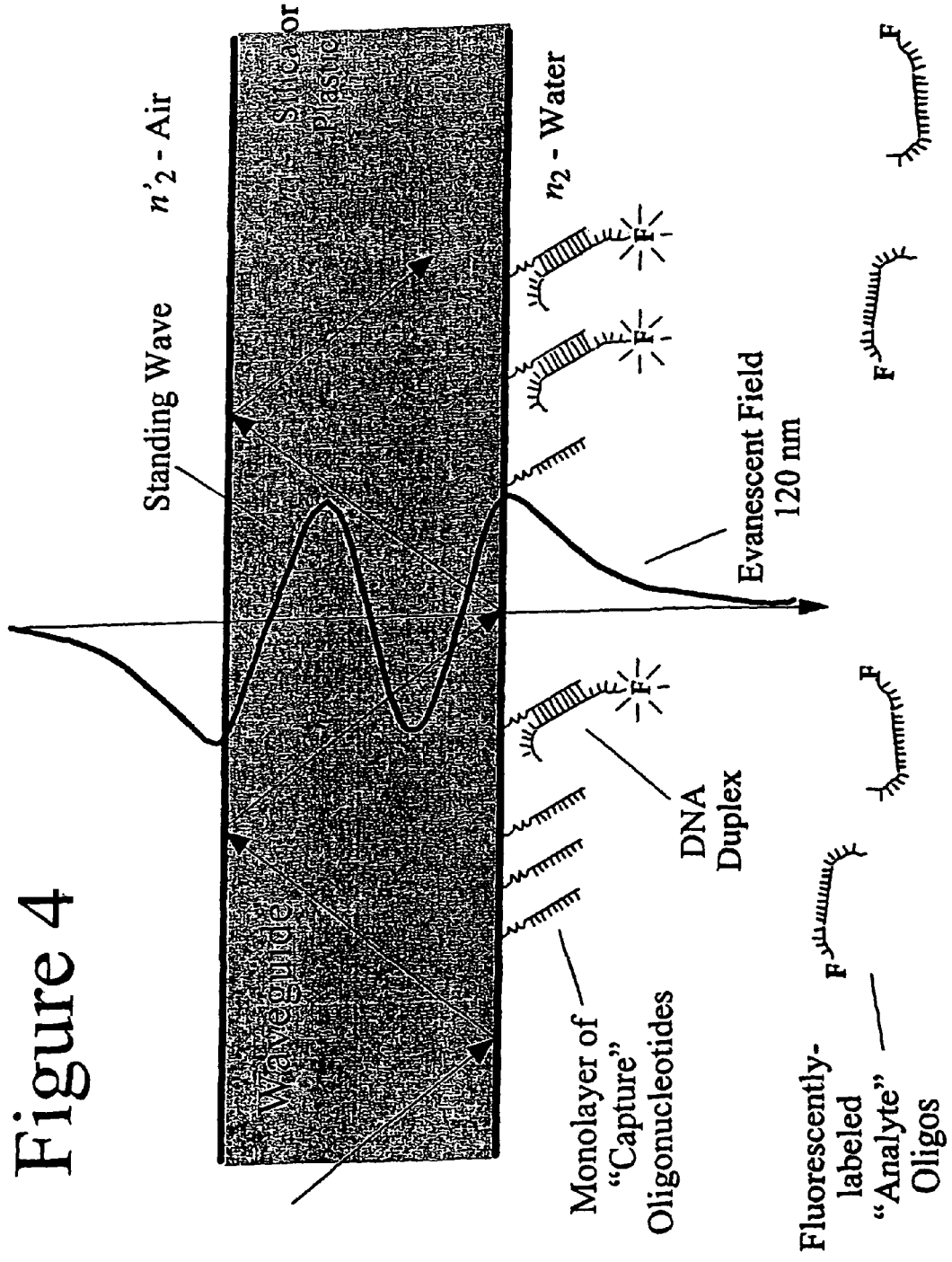
FIG. 4 illustrates an exemplary planar waveguide showing an evanescent field created by refracted light, stretching about 120 nm from the waveguide's surface to excite fluorescently labeled analytes.

The hybridization assay is schematically represented in FIG. 4. A plurality of single-stranded capture probes are immobilized on the planar waveguide and soluble, single-stranded analytes are fluorescently labeled at their 5' ends with Cy5. The analytes diffuse through bulk solution and hybridize with the capture probes. Although the size of the duplex DNA formed by the hybridization event varies with the size of the analyte, the duplex DNA is generally smaller than the penetration depth (approximately 110 nm) of the evanescent field of the biosensor system. Once hybridized, the analytes are selectively excited by the evanescent field, producing a fluorescent signal. The signal is collected through an interference filter (670 nm, Omega Optical, Inc., of Brattleboro, Vt.) and is detected by a CCD camera (Model ST-6 Opto-head, Santa Barbara Instrument Group of Santa Barbara, Calif.) oriented such that its collection axis is normal to the plane of the waveguide.

Injection-molded planar waveguide sensors were fabricated from polystyrene by Opkor, Inc. of Rochester, N.Y. These sensors were integrated optical devices consisting of a 25×25×0.5 mm planar waveguide and a light coupling lens (inclined at approximately 20° to the plane of the waveguide), molded as a single piece. The light source was a 15 mW semiconductor laser that emitted at 638 nm. Laser light was formed into a sheet beam (20 mm×1 mm) with a negative focal length lens and coupled into the waveguide via the integrated coupling lens. Once coupled, the light traversed the length of the planar waveguide, bouncing back and forth between the surfaces of the waveguide (i.e., "internal reflection"). At each reflection point, the light creates a standing wave within the planar waveguide. This standing wave does not have a sharp boundary at the waveguide surface, but instead tunnels a few hundred nanometers into the surrounding medium. The intensity of this so-called "evanescent" field decays exponentially as it penetrates into the surrounding medium.

Planar waveguide biosensors have the potential for continuous data acquisition in real-time. However, the data collection procedure (described below) had a sampling period of 6 seconds, allowing about 10 data points to be collected per minute. Although not continuous, this was adequate for monitoring hybridization kinetics in the nanomolar concentration range. Another advantage of kinetic measurements is that they allow a greater degree of precision than could be achieved with a single end point measurement. Kinetic measurements also provide information about the shape (i.e., kinetics profile) of the hybridization curve, which can be exploited to detect mismatched bases in duplex DNA. Finally, kinetic measurements are inherently insensitive to the native fluorescence of the polystyrene waveguide material, thereby reducing a source of assay noise.

The data collection cycle consisted of the following four acts. The controlling computer (Power Macintosh Performa model 6360, Apple Computer) first instructed the CCD camera to take a "dark image" of the planar waveguide with the shutter closed and the light source off. This dark image was used to correct for background noise. A "light image" was then taken of the waveguide with the shutter open and the light source turned on. The dark image was then subtracted from the light image to give the signal. Individual pixels were summed ("binned") over the three channels of the waveguide to give an intensity value for each zone. This cycle was repeated twenty times at 6 second intervals, giving 21 data points in just over two minutes. LabView version 4.0.1 software (1996), available from National Instruments Corp. of Austin, Tex., was used for all instrument control operations.

Kinetic data was subjected to a two-parameter nonlinear curve fitting procedure to obtain the intercept ($A_0$) and the average hybridization rate ($A_1$) of the hybridization kinetics curve. The following kinetics model was found to fit the hybridization data where Y is fluorescence intensity, k is a user defined curve shape factor (0.3 for all experiments, $t_{mid}$ is the midpoint time of the data collection interval, and t is time):

$$Y = A_0 + A_1 \left( \frac{e^{kt_{mid}}}{k} \right)(1 - e^{-kt}) \qquad (1)$$

For each solution, several hybridization reactions, each at a different temperature, were preformed. The slope or rate of the hybridization reaction is graphed against the temperature, and is used to extrapolate a 'zero slope' temperature, or melting point for a particular sequence.

Figure 5:
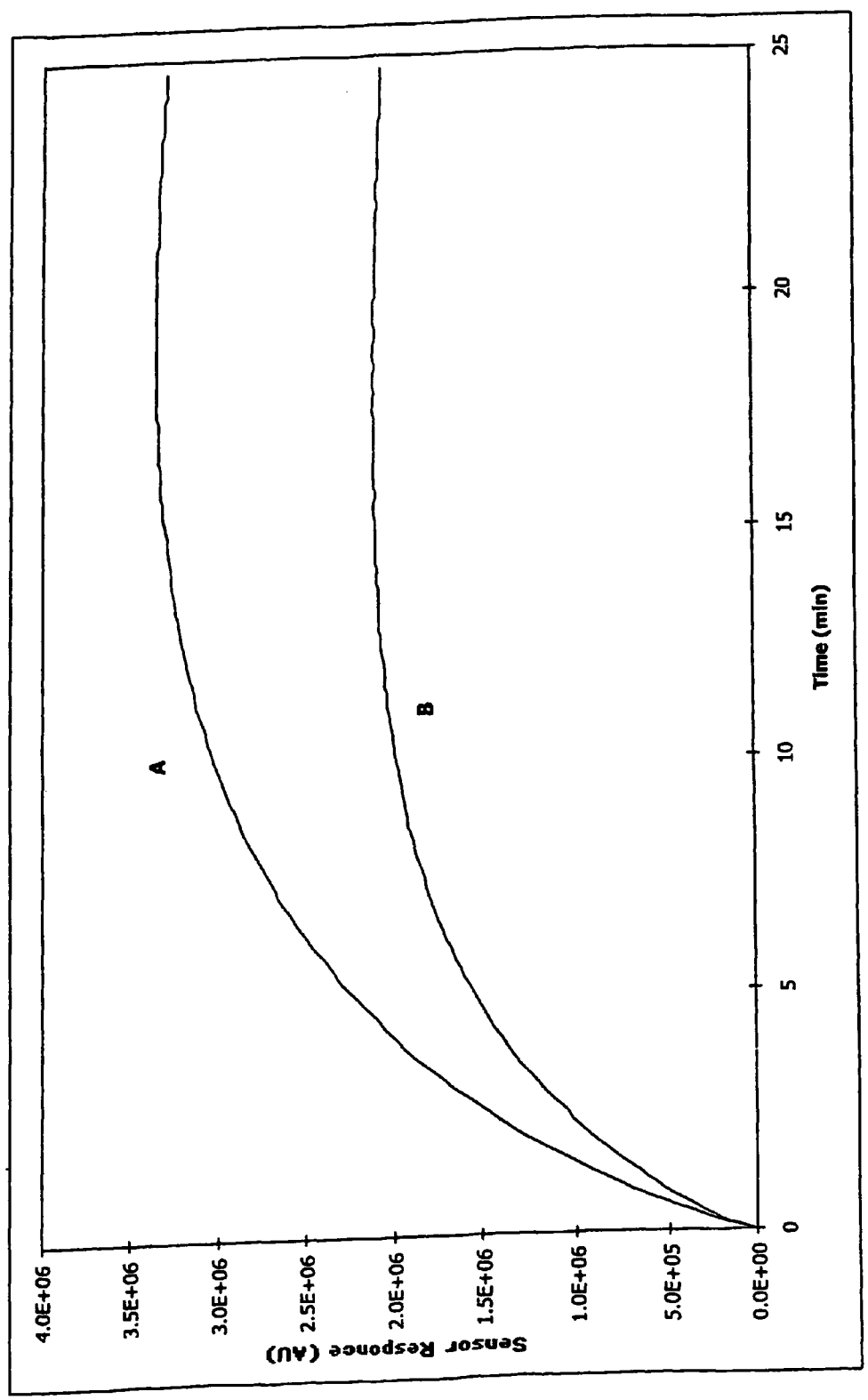
FIG. 5 shows biosensor response curves comparing the time to equilibrium of a perfectly matched DNA duplex (plot A) and a single base pair mismatch (plot B). Both 21-mers were at a concentration of 1E-10, run at 32° C., in a solution of 74 mM NaCl, 80 mM KCl, 1 mM $MgCl_2$, and 1 mM $CaCl_2$, 10 mM Tris at a pH of 8.5. Readings were taken every 20 seconds.

As shown in FIG. 5, the duplex formation for the wildtype (plot A) and the G760A (plot B) analytes have different thermodynamics, but similar kinetics. Typical hybridization kinetics curves for the binding of 100 pM Cy5-labeled analytes to immobilized capture probes at 32° C. are shown. The curve shape is indicative of a first order reaction in that the initial hybridization rate is high but decreases continuously as the reaction approaches equilibrium. In particular, the equilibrium concentration of double-stranded DNA (sensor response is proportional to double-stranded DNA concentration) is greater for the homoduplex than for the heteroduplex, but both reactions require about the same amount of time to reach equilibrium. The hybridization reaction is pseudo-first order because the solution concentration of analyte DNA is limiting since the capture probe is present in more than a 100-fold mole excess over the analytes. The curvature is most pronounced at times longer than 2 minutes or at elevated temperatures (data not shown). As shown in Table 1, there is good differentiation between the wildtype (plot A) and the G760A (plot B) analytes at very short times or very long times. However, at the short time periods, there is poor accuracy because of over dependence on the first few points.

TABLE 1

Effect of evaluation time ($t_{mid}$) on $A_1$ (hybridization rate) for data shown in FIG. 5.

| | Wildtype (Plot A) | SNP (Plot B) | $A_{1WT}/A_{1SNP}$ |
|---|---|---|---|
| $t_{mid} = 0$ | 7.10E+05 | 3.73E+05 | 1.90 |
| $t_{mid} = 1$ | 5.73E+05 | 5.00E+05 | 1.15 |
| $t_{mid} = 2.5$ | 4.16E+05 | 3.21E+05 | 1.30 |
| $t_{mid} = 12.5$ | 4.91E+04 | 1.66E+04 | 2.96 |
| $t_{mid} = 25$ | 3.40E+03 | 407 | 8.35 |

The values of k and $A_0$ were independent of $t_{mid}$. For plot A: k=0.21, $A_0$=3.86E+6; for plot B: k=0.30, $A_0$=3.10E+6.

Due to the pseudo-first order nature of the kinetic curves, a first-order model (equation (1)) was derived based on the assumption of limiting analyte concentration for fitting fluorescence intensity versus time data. Equation (1) has three parameters: intensity intercept $A_0$, hybridization rate $A_1$, and technical rate constant k. The latter can also be viewed as an empirical shape factor, k, that describes the degree of curvature to the kinetics curve. As k approaches zero, the line becomes linear. The intercept value ($A_0$) is the initial intensity response of the sensor (immediately after analyte is injected into the flowcell). It is due to factors such as native fluorescence of the waveguide, leakage of scattered laser light through the interference filter, and excitation of unbound Cy5-labeled analyte in bulk solution by scattered laser light. Although not directly relevant to the hybridization reaction being monitored, it may be used to provide quality control information about the waveguides and/or light collection system. The hybridization rate value ($A_1$) is an average rate value (based on all data points) evaluated at a midpoint time ($t_{mid}$) of the curve. Equation (1) was fit to the hybridization kinetic data sets shown in FIG. 5 using non-linear least squares. The results are shown in Table 1 using different midpoints to evaluate $A_1$. The greatest differentiation between wildtype and SNP binding is at very short or very long times. At very short times there is a high dependence on the first few points, leading to decreased precision. However, having to wait for longer times defeats the purpose of a fast assay. A good compromise of assay time and precision is at 1 minute on a two minutes assay.

Non-linear curve fitting is a numerical procedure and requires a few seconds for the successive iterations to converge. Thus, it is not really suitable for real time fitting of hybridization kinetic data. However, equation (1) may be linearized by fixing the shape factor and defining a parametric time variable (Z) as shown in equations (2) and (3) below:

$$\text{For Constant } k, Z = e^{-kt} \quad (2)$$

$$Y = A_0 + A_1\left(\frac{e^{kt_{mid}}}{k}\right)(1-Z) = \left(A_0 + \frac{A_1 e^{kt_{mid}}}{k}\right) - \left(\frac{A_1 e^{kt_{mid}}}{k}\right)Z \quad (3)$$

In order for this linearization to be successful, shape factor k needs to be either fairly uniform between data sets or only weakly coupled to hybridization rate $A_1$. Plots A and B in FIG. 5 exhibited k values of 0.21 min$^{-1}$ and 0.30 min$^{-1}$, respectively. Plot B showed more curvature, but reached a lower equilibrium sensor response. Over a broader range of data sets, the shape factor varied from 0 to 0.5. Thus, it was not particularly constant between data sets.

Figure 6:
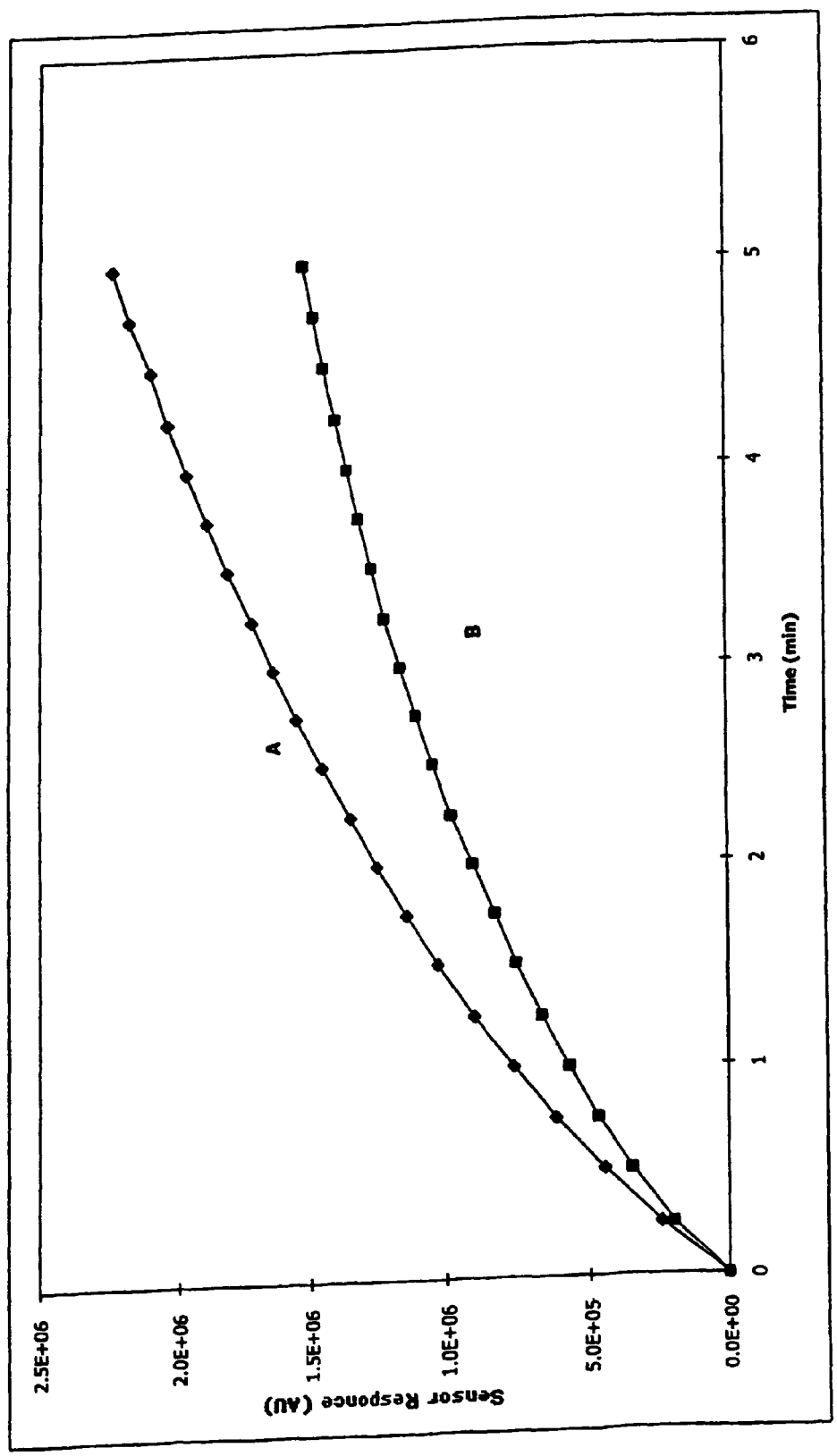
FIG. 6 shows an exploded plot of the first 21 points (5 minutes) of FIG. 5.

The degree of coupling between the shape factor and hybridization rate are examined in FIG. 6 and Tables 1 and 2. The plots shown in FIG. 6 are exploded views of the first five minutes of the hybridization kinetics curves presented in FIG. 5. To achieve a fast (<5 minute) SNP assay, the first five minutes of the reaction were focused on because the hybridization kinetics of the wildtype and polymorphic sequences are well differentiated during this period. True three parameter ($A_0$, $A_1$, k) fits both data sets (homoduplex and heteroduplex) are shown in Table 2.

TABLE 2

Figure 7:
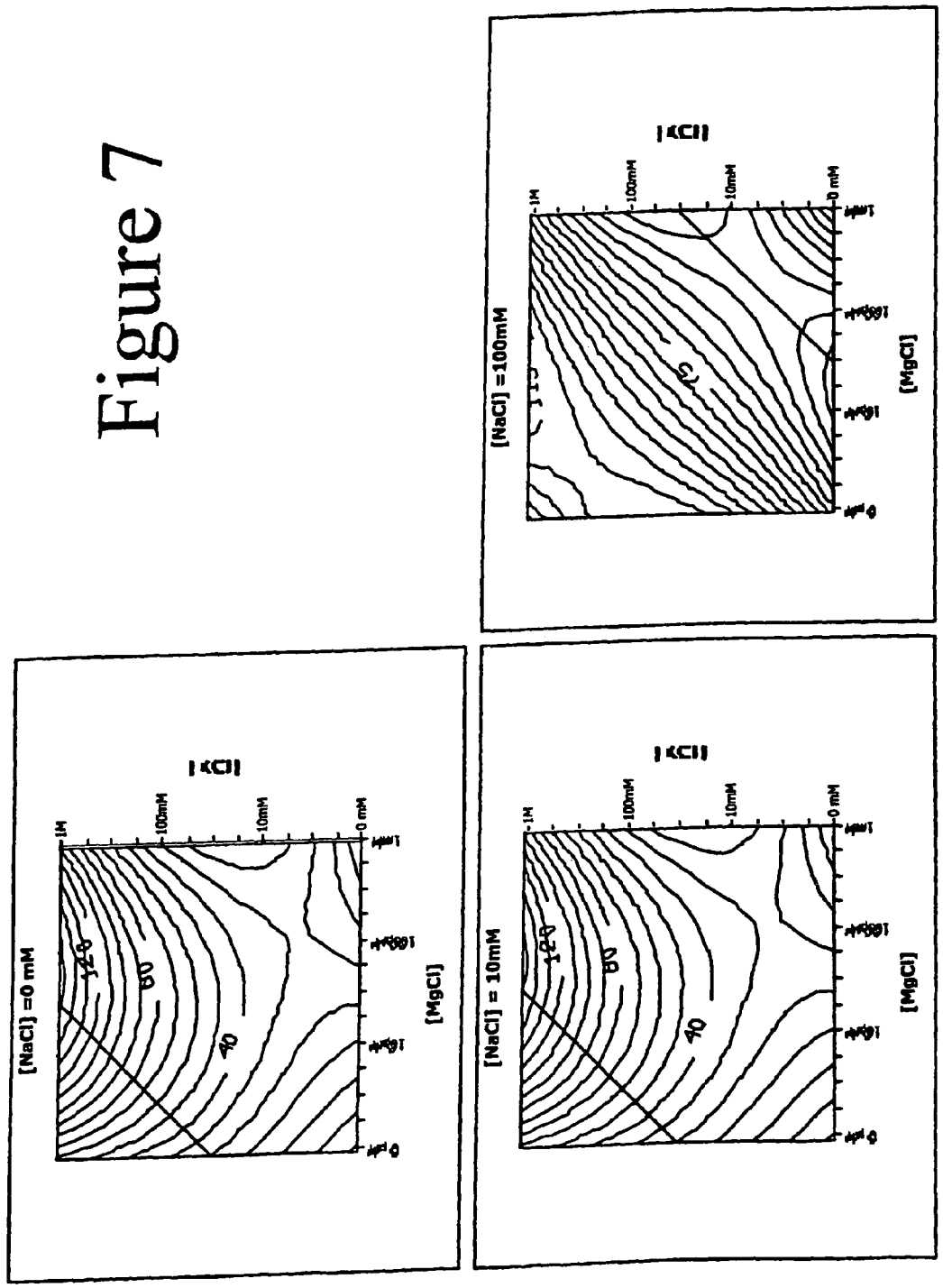
FIG. 7 illustrates a contour map depicting the typical sensor response of the perfectly matched DNA duplex 2° C. below the melting point of the duplex. $MgCl_2$ and KCl concentrations were varied while NaCl concentration was held fixed at 0M (top), 10 mM (middle), or 100 mM (bottom)

Effect of shape factor (k) on computed value for hybridization rate for the data shown in FIG. 7. A midpoint time ($t_{mid}$) of 2.5 minutes was used in all cases.

| | k | $A_0$ | $A_1$ | Error in $A_1$ | $r^2$ |
|---|---|---|---|---|---|
| Wildtype | | | | | |
| 3-Parameter fit | 0.26 | 3.82E+06 | 4.04E+05 | | 0.9996 |
| k = 0.1 | 0.10 | 3.99E+06 | 4.17E+05 | 3.2% | 0.9935 |
| k = 0.2 | 0.20 | 3.88E+06 | 4.12E+05 | 2.0% | 0.9987 |
| k = 0.3 | 0.30 | 3.79E+06 | 3.98E+05 | 1.5% | 0.9993 |
| k = 0.4 | 0.40 | 3.70E+06 | 3.75E+05 | 7.2% | 0.9957 |
| k = 0.5 | 0.50 | 3.63E+06 | 3.47E+05 | 14.1% | 0.9885 |
| SNP | | | | | |
| 3-Parameter fit | 0.37 | 3.05E+06 | 3.03E+05 | | 0.9991 |
| k = 0.1 | 0.10 | 3.27E+06 | 3.26E+05 | 7.6% | 0.9827 |
| k = 0.2 | 0.20 | 3.18E+06 | 3.24E+05 | 6.9% | 0.9927 |
| k = 0.3 | 0.30 | 3.11E+06 | 3.14E+05 | 3.6% | 0.9980 |
| k = 0.4 | 0.40 | 3.03E+06 | 2.98E+05 | 1.7% | 0.9990 |
| k = 0.5 | 0.50 | 2.96E+06 | 2.77E+05 | 9.4% | 0.9962 |

The two data sets were then analyzed using the two-parameter fit (equation (3)) for several pre-selected values of k between 0.1 and 0.5.

The results of Table 2 show that while no singe k value gives perfect results, a value of 0.3 was a good compromise, giving a worse case error of 3.6% in hybridization rate. Thus, it appears that hybridization rate is only weakly coupled to the shape factor. For this reason, shape factor k was fixed at 0.3 in all subsequent experiments. Also with only two variables to calculate, we were able to perform a real time calculation of the slope.

The data shown in FIG. 5 was obtained in a standard PCR buffer at 32° C., which is well below the melting temperatures of the homoduplex (approximately 55° C.) and heteroduplex (approximately 53° C.). To achieve a quicker and more accurate assay, the assay conditions were optimized for greater differentiation between the wildtype and G760A analytes.

Figure 8:
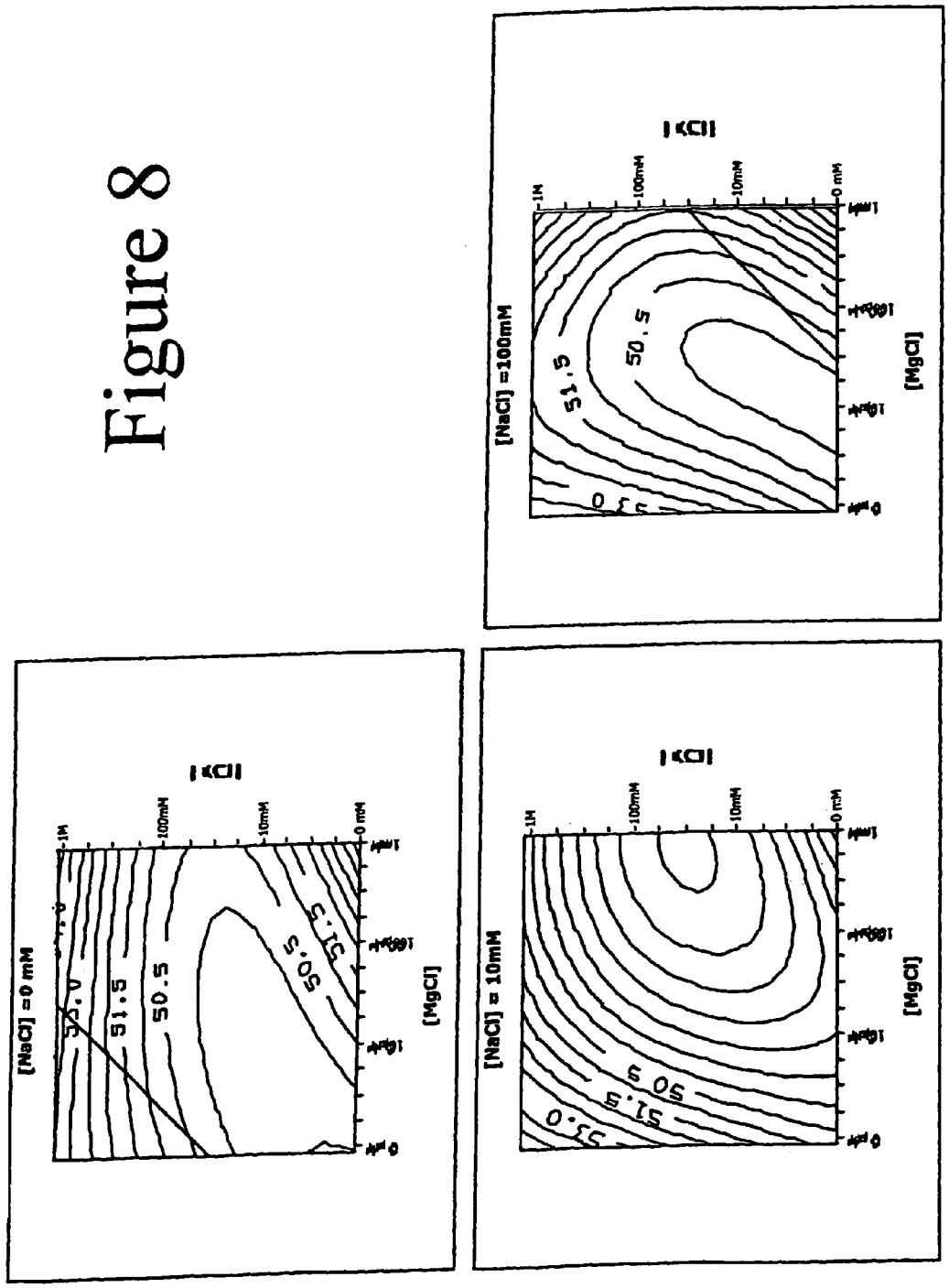
FIG. 8 is a contour map showing the melting point of a perfectly matched DNA duplex as it changes with salt concentration. $MgCl_2$ and KCl concentrations were varied while NaCl concentration was held fixed at 0M (top), 10 mM (middle), or 100 mM (bottom)

Since the hybridization rate is dependent on the counter ion concentration and melting temperature range, both of these factors were optimized in concert. Both the hybridization rate and the melting temperature of a DNA duplex are dependent upon ion concentration. The effect of ion concentration on the hybridization rate is shown in FIG. 7. The effect of ion concentration on melting temperature is shown in FIG. 8. In each of these figures the effects of sodium are only shown at three values, while the effects of magnesium and potassium are continuous within the specified range.

Figure 9:
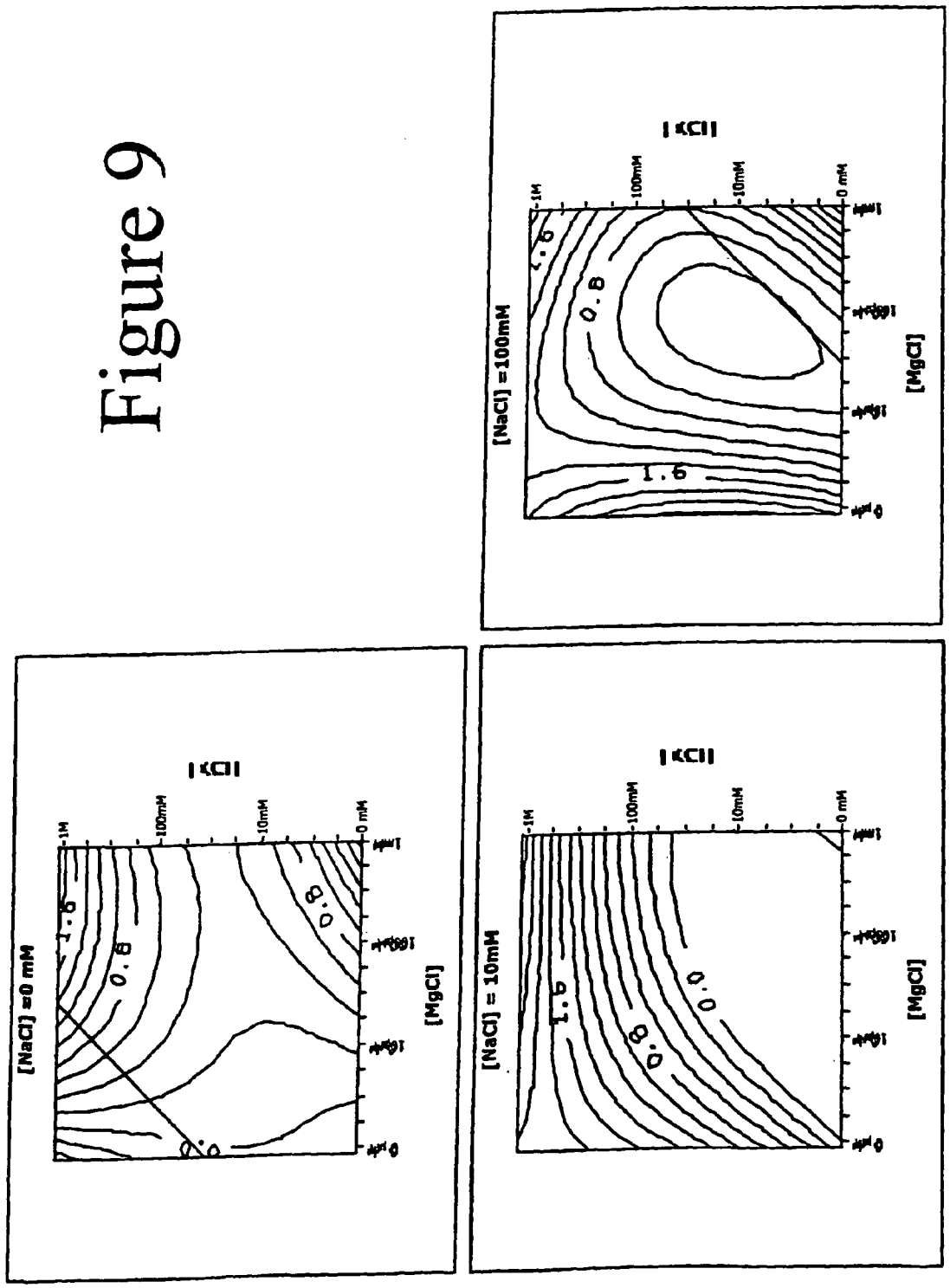
FIG. 9 is a contour map depicting the difference between the melting point of the perfectly matched DNA duplex and that of a DNA duplex with one base pair mismatch (in ° C.). $MgCl_2$ and KCl concentrations were varied while NaCl concentration was held fixed at 0M (top), 10 mM (middle), or 100 mM (bottom)

With mixtures of counter ions, the results can be diverse and unpredictable. Sometimes addition of one ion masked the effects of another ion (FIG. 9 plot B, sodium attenuates the effect of magnesium on $\Delta T_m$); sometimes two ions had a synergistic effect (FIG. 7 plot B, greatest slope at 1M potassium and 100 μM magnesium), and sometimes they competed with each other (FIG. 7 plot C, addition of magnesium and potassium in 1:1000 ratio has no effect on slope). At some concentrations, it seemed that one ion mainly determined the melting temperature (FIG. 8 plot B, magnesium), while the other determined the hybridization rate (FIG. 7 plot B, potassium). The mechanisms of ionic effects on DNA hybridization are many, from stabilization of the backbone, to the ions forming a bridge between hydrogen bonds of zipping or unzipping strands.

Figure 10:
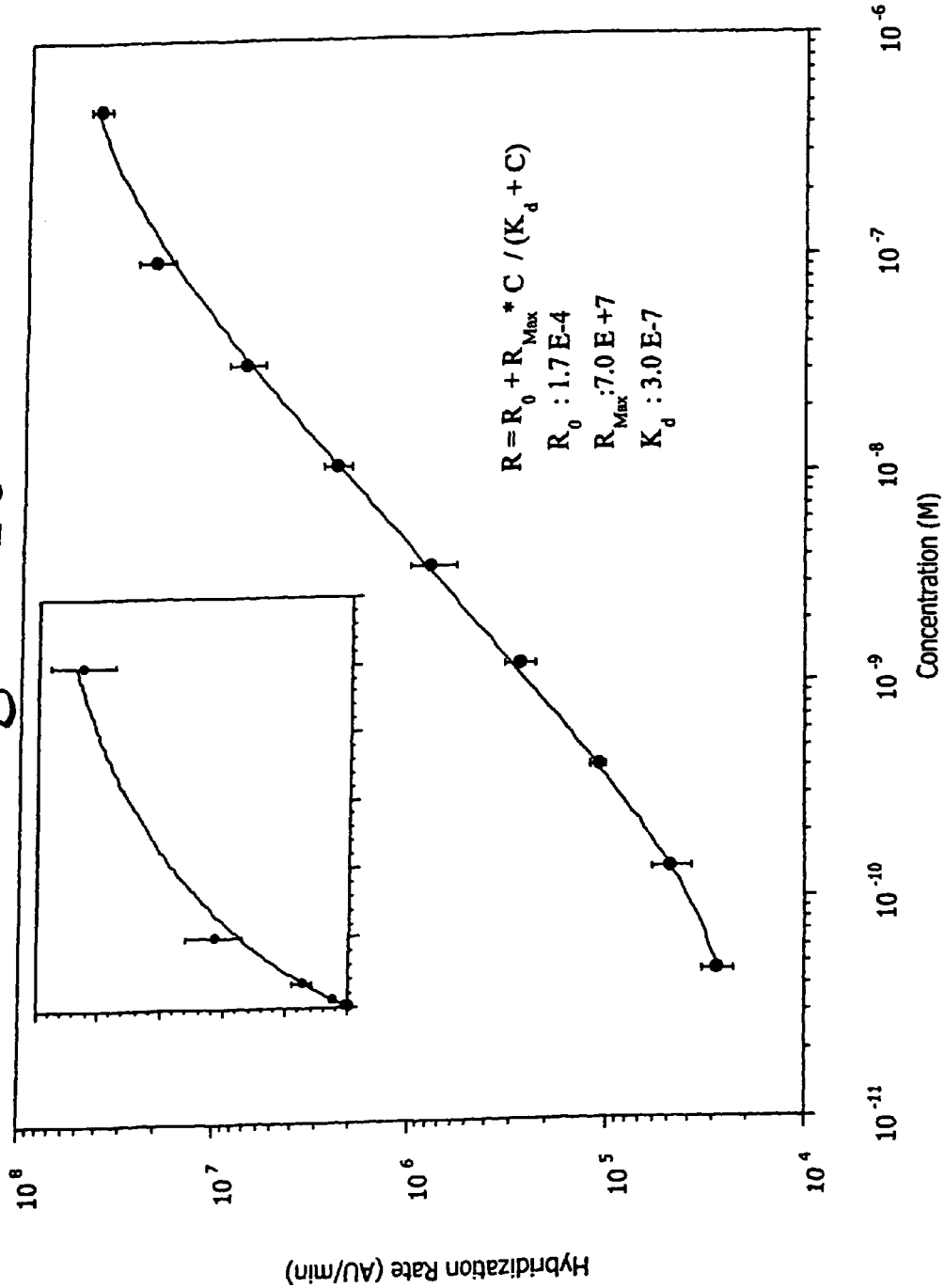
FIG. 10 shows biosensor output versus concentration of injected DNA, showing the calculation of the detection limit of the sensor. Conditions were 10 mM Tris, 40 mM NaCl, 1.5 mM MgCl2, pH 8.8, and at 25° C. Slope of the curve is 3.3E+16 Molar/AU and the standard deviation of the zero is 9E+3 AU, making the detection limit 66 picomolar.

Hybridization rate decreased with several factors including labeled DNA concentration, counter ion concentration, and temperature. As the signal went down, the signal-to-noise ratio also degraded, giving less reliable data. The detection limit of a hybridization assay may be determined from a standard curve of hybridization rate versus analyte oligonucleotide concentration and with the background noise (standard deviation of the zero concentration point) as defined by NCCLS. Such a determination is shown in FIG. 10 for a hybridization assay for the wildtype analyte performed under conditions commonly used in PCR reactions: 10 mM Tris, 40 mM NaCl, 1.5 mM $MgCl_2$, pH 8.8, and at 25° C. Under these conditions, the calculated detection limit was 34 picomolar.

The relative success of a given set of counter ion concentrations was evaluated by measuring the difference between the melting points of the homo- and heteroduplexes. Many standard buffers (such as PCR buffers) gave good results. In order to increase the difference in melting temperatures ($\Delta T_m$), the optimizing program MultiSimplex was used to systematically vary the concentrations of NaCl, KCl, and $MgCl_2$. After several iterations, a range of ion concentrations was identified that gave us primarily non-zero $\Delta T_m$ values.

The ECHIP program was used to generate contour maps of $\Delta T_m$ versus counter ion concentration. Such plots are more informative than simply determining the absolute $\Delta T_m$ maxima because they provide information about the inherent relationships between $\Delta T_m$ and counter ion concentration. The parameters of the ECHIP calculation were as follows. The concentration ranges for KCl were 0-1000 mM, for NaCl were 0-100 mM, and for $MgCl_2$ were 0-1000 μM. The analysis of the data obtained for ECHIP was fitted to a partial cubic equation. The partial cubic equation required additional data than other types in order to test more complex interactions between the variables (ion concentrations).

The results of the ECHIP experiments are shown in FIG. 9. These plots are three-dimensional representations of $\Delta T_m$. One ion concentration is held constant in each of three plots while the effect on $\Delta T_m$ is shown in relation to the other two. For simplification, values of $\Delta T_m$ less than 0.5° C. were set to zero, as we were trying to maximize $\Delta T_m$. The greatest $\Delta T_m$ value observed within the counter ion concentration range examined was about 2.5° C.

In the absence of sodium (FIG. 9A), $\Delta T_m$ increased steadily with increasing magnesium concentration at either low or high concentrations of potassium. At intermediate potassium concentrations, magnesium had little effect. At a low sodium concentration (10 μM), as shown in FIG. 9B, magnesium again seemed to have little effect on $\Delta T_m$, which depended primarily on potassium concentration. However, at higher sodium concentrations (100 μM, shown in FIG. 9C), the $\Delta T_m$ curve had a concave shape. At intermediate concentrations of magnesium and potassium, the competitive effect between the ions seemed to mask any melting point differential between the wildtype and polymorphic sequences. It was only at very high or very low concentrations that significant differentiation of the two Tm values was obtained.

The range of temperatures that yielded optimal results for this assay was important, as was the detection limit. As the hybridization rate increased, the detection limit also improved. FIG. 7 shows the hybridization rate of the perfectly matched duplex 2 degrees below the melting temperature. Comparing FIG. 7 to FIG. 9, as it is different aspects of the same data, shows that ion concentrations may have different effects on the hybridization rate and the change in melting temperature.

The hybridization rate of the SNP and the wildtype oligonucleotide were comparable (within a factor of 10) to each other only one degree below the melting point of the wildtype. In other words, lower than one degree below the melting point of the SNP, there was little or no differentiation.

Example 5

SBH was used to resequence regions of the KVLQT1 gene. The following buffers were used in the experiments. Phosphate buffer saline ("PBS") (40 mM phosphate, 100 mM sodium chloride, 0.02% sodium azide, pH 7.4) was used for coating neutravidin on the polystyrene surfaces on the planar waveguide. Tris EDTA ("TE") (10 mM Tris base, 1 mM EDTA, pH 7.4) was used for washing steps. DNA binding buffer (TE with 800 mM potassium chloride, 74 mM sodium chloride, 1 mM calcium chloride, and 1 mM magnesium chloride, pH 8.5) was used. TE with 0.1% trehalose was used for postcoating the surfaces of the planar waveguide. These reagents were all purchased from Sigma Chemical Co. (St. Louis, Mo.).

All DNA samples were synthesized at the DNA and Peptide Synthesis Facilities, University of Utah, headed by Dr. R. W. Schackmann. A capture probe with the following sequence was synthesized:

```
Capture probe:
  5'-G GAG CCC AGG-3'-biotin (C10)    SEQ ID NO:8
```

Four analyte probes derived from the LQTS gene portion were synthesized. The analyte probes have the following sequences:

```
5'-CCT GGG CTC CGT GGT CTT CAT-3'    SEQ ID NO:9
(P1)

5'-CCT GGG CTC CAT GGT CTT CAT-3'    SEQ ID NO:10
(P2)

5'-CCT GGG CTC CCT GGT CTT CAT-3'    SEQ ID NO:11
(P3)

5'-CCT GGG CTC CTT GGT CTT CAT-3'    SEQ ID NO:12
(P4)
```

Sequencing probes, labeled with Cy5, with the following sequences were synthesized.

```
degenerate probes:
(X = equal mixture of A, C, G, T)

CXXXX-cy5   (pc)                    SEQ ID NO:13

TXXXX-cy5   (pt)                    SEQ ID NO:14

GXXXX-cy5   (pg)                    SEQ ID NO:15

AXXXX-cy5   (pa)                    SEQ ID NO:16 nondegenerate probes:               SEQ ID NO:17

CACCA-cy5   (spc)                   SEQ ID NO:18

TAGCA-cy5   (spt)                   SEQ ID NO:19

GACCA-cy5   (spg)                   SEQ ID NO:20

AACCA-cy5   (spa)                   SEQ ID NO:21
```

Clean polystyrene planar waveguides (1×1 inch), with an integral front lens for excitation light and a knife edge back lens for the prevention of back reflection of the light, were coated with neutravidin (1.5e-7 M, PBS) at room temperature for 60 min with the help of a gasket. After 3 washes with TE, the planar waveguide was coated with C10 (1e-7 M, TE)(SEQ ID NO: 8) at room temperature for another 60 min. After 2 washes with TE, the surface of the planar waveguide was postcoated with TE with 0.1% trehalose at room temperature for 30 min. The postcoating solution was discarded and the planar waveguide was dried in a vacuum chamber with the gasket attached.

The capture probe (C10) (SEQ ID NO:8) immobilized through neutravidin on the waveguide surface was incubated with one of the 4 analyte probes (P1, P2, P3, or P4 (SEQ ID NOS: 9-12, respectively), 5e-10 M, binding buffer, 4° C., 10 min.). To start the assay, a solution of the labeled, sequencing probe was injected into the flowcell. As soon as the hybridization started, the fluorescent dye captured onto the waveguide surface within the evanescent field thickness started to emit fluorescence under the laser excitation. The fluorescence emission was detected using an optical system and a CCD camera. The CCD camera recorded waveguide images at 15 second intervals over a 5 min. period. An operational program written in LabView software (Assay StandAlone 1.2 Side) was used to operate the sample injection with a Cavro pump, fluorescence image recording by the CCD camera and the data transfer. The data reflecting rapidly increasing of the fluorescence which is changing non-linearly with time were the result of the average rate of the analyte binding ($R_{t_s}$) at a particular point of time ($t_i$), given by equation (4):

$$I(t_i) = R_{t_s}\left(\frac{e^{kt_s}}{k}\right)(1 - e^{-kt_i}) + I_0 \quad (4)$$

where I(t) is the sensor's fluorescence intensity response. Once the average rate had been computed, it could be used to construct a standard curve. In general, the Michaelis-Menton equation could be used to binding rate versus analyte concentration data:

$$R_c = R_0 + \frac{R_{max}C}{K_d + C} \quad (5)$$

where $R_c$ was the hybridization rate observed for oligonucleotide at concentration C, $R_{max}$ was the maximum possible hybridization rate, $R_0$ was the rate in the absence of analyte, $K_d$ was the apparent Michaelis constant. When $C \ll K_d$, this equation simplifies to a linear expression for analyte concentrations:

$$R_c = R_0 + \frac{R_{max}}{K_d}C \quad (6)$$

Figure 11A:
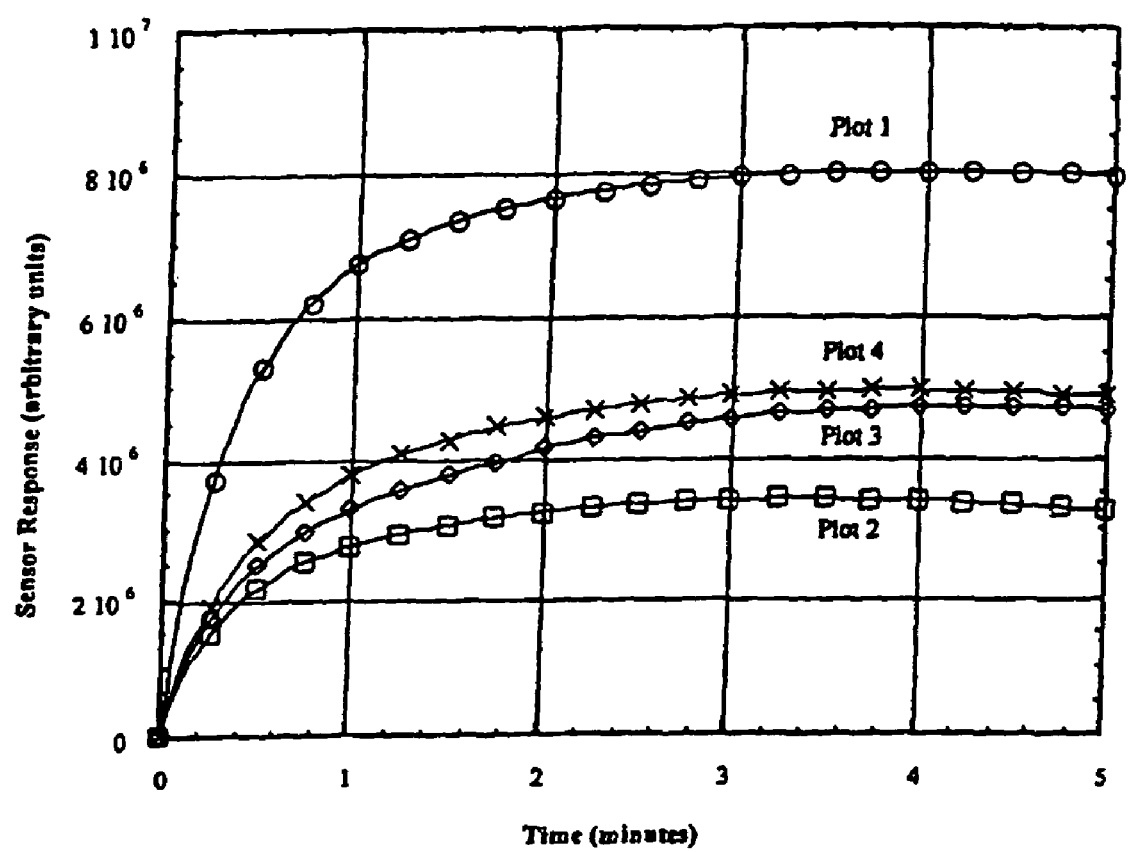
FIG. 11A shows hybridization kinetics curves for sequencing by hybridization of the middle ($11^{th}$) position of analyte probe P1 (SEQ ID NO: 9). The capture probe ($C10PO_4$) contained a 5' phosphate group. Four different degenerate Cy5-labeled sequencing probes (pc, pt, pg, pa) (SEQ ID NOS: 13-16, respectively) were used. Plot 1 is the hybridization kinetics of the wildtype sequencing probe (CXXXX-Cy5) (SEQ ID NO: 13). Plots 2-4 are the hybridization kinetics for single base mismatches in which the 5' nucleotide of the sequencing probe were A, G & T, respectively.
Figure 11B:
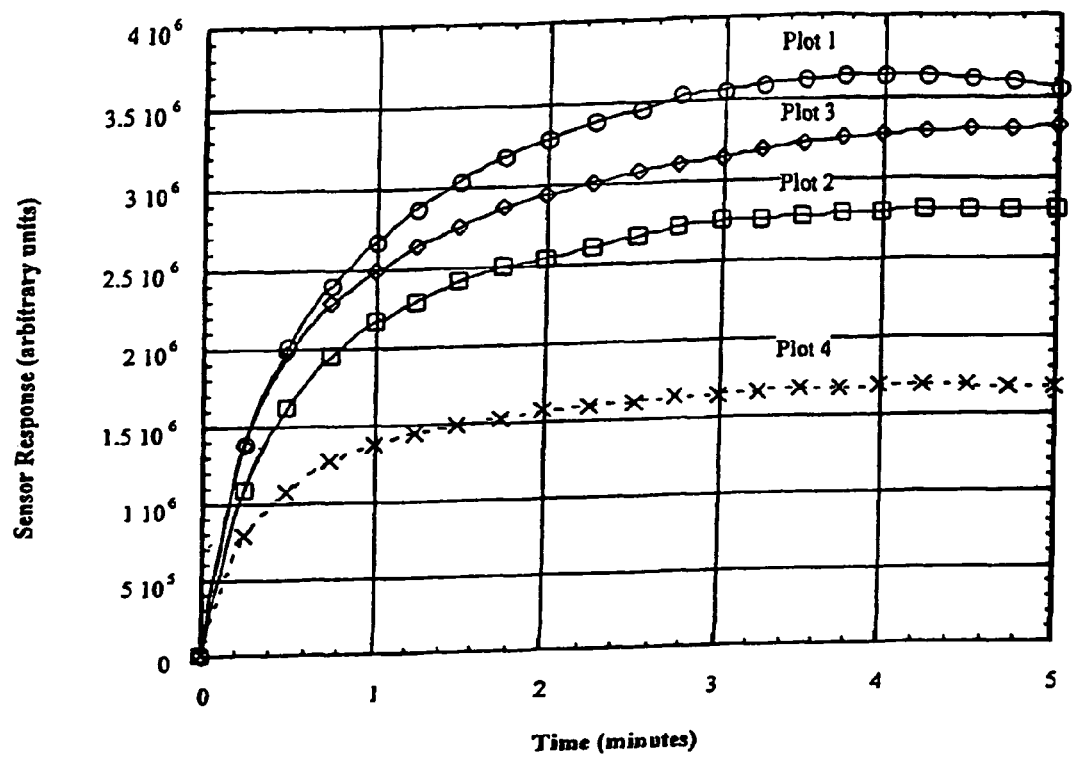
FIG. 11B shows hybridization kinetics curves for sequencing by hybridization of the middle ($11^{th}$) position of analyte probe P1(SEQ ID NO: 9). The capture probe (C10) (SEQ ID NO: 8) contained a 5' hydroxyl group in this case. Four different degenerate Cy5-labeled sequencing probes (pc, pt, pg, pa) (SEQ ID NO: 13-16, respectively) were used. Plot 1 is the hybridization kinetics of the wildtype sequencing probe (CXXXX-Cy5) (SEQ ID NO: 13).Plots 2-4 are hybridization kinetics for single base mismatches in which the 5' nucleotide of the sequencing probe were A, G & T, respectively.

The hybridizations between the capture probe C10 (SEQ ID NO: 8) and the 4 analyte probes derived from the LQTS gene portion, P1, P2, P3, or P4, (SEQ ID NOS: 9-12, respectively), are the same. The SNP is the $11^{th}$ position. For P1, the SNP is G, so two of the eight sequencing probes, CXXXX-Cy5 (pc) (degenerate) (SEQ ID NO: 13) or CACCA-Cy5 (spc) (nondegenerate) (SEQ ID NO: 17), make the complete complimentary 15-mer DNA duplex. This is the perfect match for all the base pairs. At the same time, P1 (SEQ ID NO: 9) would not give complete hybrids between C10 (SEQ ID NO: 8) and the other sequencing probes. In those cases, the pairs would be mismatched. The measurements of the emitted fluorescence during the hybridization on the waveguide surfaces showed that the perfect match pairs always gave a higher reaction rate and a net increase of fluorescence (in number of photon counts). FIGS. 11a and b show typical curves of the hybridization process expressed in the measured net increase of fluorescence in photon counts versus time, measured in minutes.

The degree of the lowering hybridization of a mismatched pair compared to a perfect match pair can be expressed in a percentage, with the perfect pair having the hybridization of 1. The percentage is known as a rejection. Tables 3 and 4 show the rejections of C10 with the 4 analyte probes with mismatching sequencing probes compared to the perfect match cases.

The immobilized capture probe (C10) (SEQ ID NO: 8) contained a 5' hydroxyl group and degenerate sequencing probes (pc, pa, pg, pt) were used. (SEQ ID NOS: 13, 16, 15, and 14, respectively) were used. Rejection factors were derived from the comparison of the rates of mismatched pairs to the perfect match pair.

TABLE 3

Hybridization rates for SBH of the middle ($11^{th}$) position of the four analyte probes (P1–P4).

| | Average rate | % Std. Dev. | Rejection |
|---|---|---|---|
| C10/P1/spc | 598358 | 19% | |
| C10/P1/spa | 576064 | 5% | 0.96 |
| C10/P1/spg | 480554 | 29% | 0.80 |
| C10/P1/spt | 86181 | 26% | 0.14 |
| C10/P2/spt | 1309221 | 34% | |
| C10/P2/spa | 338359 | 19% | 0.26 |
| C10/P2/spc | 818384 | 12% | 0.63 |
| C10/P2/spg | 513525 | 55% | 0.39 |
| C10/P3/spg | 913465 | 40% | |
| C10/P3/spa | 326183 | 34% | 0.36 |
| C10/P3/spc | 470079 | 25% | 0.51 |
| C10/P3/spt | 614313 | 49% | 0.67 |

TABLE 3-continued

Hybridization rates for SBH of the middle (11$^{th}$)
position of the four analyte probes (P1–P4).

|  | Average rate | % Std. Dev. | Rejection |
| --- | --- | --- | --- |
| C10/P4/spa | 1032881 | 20% |  |
| C10/P4/spc | 214920 | 17% | 0.21 |
| C10/P4/spg | 463645 | 18% | 0.45 |
| C10/P4/spt | 214049 | 19% | 0.21 |

The capture probe (C10) (SEQ ID NO: 8) contained a 5' hydroxyl group in this case. Nondegenerate sequencing probes (spc, spa, spg, spt) (SEQ ID NO: 17, 20, 19, and 18, respectively) were used in this case. Rejection factors were derived from the comparison of the rates of mismatch pairs to the perfect match pair.

TABLE 4

Hybridization rates for sequencing by hybridization
of the middle (11$^{th}$) position of four different
analyte oligonucleotides (P1–P4).

|  | Average Rate | % Std. Dev. | Rejection |
| --- | --- | --- | --- |
| C10/P1/pc* | 1960174 | 29% |  |
| C10/P1/pa | 1431129 | 28% | 0.73 |
| C10/P1/pg | 1591074 | 31% | 0.81 |
| C10/P1/pt | 937559 | 35% | 0.48 |
| C10/P2/pt* | 2616848 | 25% |  |
| C10/P2/pa | 732486 | 11% | 0.28 |
| C10/P2/pc | 1221310 | 25% | 0.47 |
| C10/P2/pg | 2091414 | 44% | 0.80 |
| C10/P3/pg* | 1843953 | 1% |  |
| C10/P3/pa | 1420362 | 35% | 0.77 |
| C10/P3/pc | 1841401 | 15% | 1.00 |
| C10/P3/pt | 2211113 | 32% | 1.20 |
| C10/P4/pa* | 1922302 | 33% |  |
| C10/P4/pc | 1325066 | 16% | 0.69 |
| C10/P4/pg | 1416990 | 32% | 0.74 |
| C10/P4/pt | 714500 | 14% | 0.37 |

*Perfect match pairs.

The effect of phosphorylating the capture probe C10 was also examined. Capture probes C10 and C10PO4 have the same sequence but C10PO4 has a phosphate group at its 5'-end. Although the phosphate group could be used for the ligation with the 5-mer sequencing probes, the ligation reaction required incubation at 4° C. for 12 h and the instant procedure monitored the hybridization only for 5 min. Therefore, the effect of phosphorylating the capture probe was examined under the latter conditions. Comparing the net increases in fluorescence and the reaction rates at 2 minutes showed that C10PO4 gave a strong hybridization response and a higher rate. The phosphate group may assist hybridization due to hydrogen bonding that is formed, although no final covalent bond built up as in the case of ligation. The rates at 2 minute of the hybridization for C10PO$_4$ with the analyte probes and sequencing probes, and corresponding rejections, are shown in Table 5 and Table 6.

The capture probe (C10PO$_4$) contained a 5' phosphate group in this case. Degenerate sequencing probes (pc, pa, pg, pt) (SEQ ID NO: 13, 16, 15, and 14, respectively) were used. Rejection factors were derived from the comparison of the rates of mismatched pairs to the perfect match pair.

TABLE 5

Hybridization rates for SBH of the middle (11$^{th}$)
position of four analyte probes (P1–P4).

|  | Average Rate | % Std. Dev. | Rejection |
| --- | --- | --- | --- |
| PO4/P1/pc | 4316220 | 10% |  |
| PO4/P1/pa | 1774543 | 24% | 0.41 |
| PO4/P1/pg | 2385418 | 11% | 0.55 |
| PO4/P1/pt | 2832229 | 23% | 0.66 |
| PO4/P2/pt | 3099725 | 15% |  |
| PO4/P2/pa | 1802958 | 20% | 0.58 |
| PO4/P2/pc | 2076006 | 22% | 0.67 |
| PO4/P2/pg | 1982273 | 16% | 0.64 |
| PO4/P3/pg | 3974225 | 13% |  |
| PO4/P3/pa | 1310945 | 23% | 0.33 |
| PO4/P3/pc | 2327110 | 21% | 0.59 |
| PO4/P3/pt | 1502286 | 24% | 0.38 |
| PO4/P4/pa | 2726077 | 11% |  |
| PO4/P4/pc | 1119316 | 9% | 0.41 |
| PO4/P4/pg | 1348100 | 19% | 0.49 |
| PO4/P4/pt | 1691061 | 24% | 0.62 |

The capture probe (C10PO$_4$) contained a 5' phosphate group. Nondegenerate sequencing probes (spc, spa, spg, spt) (SEQ ID NO: 13, 16, 15, and 14, respectively) were used. Rejection factors were derived from the comparison of the rates of mismatched pairs to the perfect match pair.

TABLE 6

Hybridization rates for sequencing by hybridization of the
middle (11$^{th}$) position of four analyte probes (P1–P4).

|  | ave. Rate | % stdev | Rejection |
| --- | --- | --- | --- |
| PO4/P1/spc | 73529 | 5% |  |
| PO4/P1/spa | 17416 | 93% | 0.237 |
| PO4/P1/spg | 33836 | 20% | 0.460 |
| PO4/P1/spt | 37274 | 11% | 0.507 |
| PO4/P2/spt | 123098 | 19% |  |
| PO4/P2/spa | 26588 | 19% | 0.216 |
| PO4/P2/spc | 25566 | 24% | 0.208 |
| PO4/P2/spg | 49364 | 29% | 0.401 |
| PO4/P3/spg | 93682 | 29% |  |
| PO4/P3/spa | 39763 | 9% | 0.424 |
| PO4/P3/spc | 20010 | 11% | 0.214 |
| PO4/P3/spt | 31770 | 31% | 0.339 |
| PO4/P4/spa | 104966 | 56% |  |
| PO4/P4/spc | 41392 | 42% | 0.394 |
| PO4/P4/spg | 25050 | 64% | 0.239 |
| PO4/P4/spt | 44766 | 70% | 0.426 |

In summary, for the C10 (SEQ ID NO: 8) and C10PO4 capture probes, each of them made 32 hybridized oligonucleotide duplexes with the four 21-mer analyte probes and the eight Cy5-labeled sequencing probes. These duplexes are in 16 groups. In each group, there is one perfect match case and three mismatches that have a difference of a single base or SNP. Using the rejection factor to express the discrimination, the average rejection factor of 0.5 clearly showed that the SNP was detected. Comparing the two C10 (SEQ ID NO: 8) and C10PO4 capture probes, the average rejection factor with the C10 (SEQ ID NO: 8) capture probe (0.58) was slightly higher than in the C10PO4 case (0.43), which showed that the phosphate group may assist in hybridization through the possible formation of a kind of hydrogen bonding. The degenerate sequencing probes have four bases, each of which is, with equal probability, one of the four nucleic acids (A, C, G, or T). For a particular DNA probe sequence there is only 1/256 chances to match to the sequence. So, the degenerate probe concentration (1e-8 M) used in the detection procedure is about 100 times higher than the concentration of nondegenerate probes (1e-10 M). However, since the degenerate probes have much higher acceptance for more DNA probes and showed a much stronger responses than the nondegenerate probes, degenerate sequencing probes are preferably used.

Example 6

In the sense of detecting a new mutant using this sequencing by hybridization method, if the sequencing probes were labeled with four different fluorescent dyes and the planar waveguide had an array of different captures, this method developed in our laboratory is definitely a very convenient and fast method.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of detecting a single nucleotide polymorphism (SNP) in a gene of interest comprising:
   immobilizing on a planar waveguide a plurality of wildtype probes and a plurality of SNP probes, wherein the wildtype and SNP probes are 15-25 nucleotides, the wildtype probes comprise sequences complementary to a wildtype sequence of the gene of interest and the SNP probes comprise sequences complementary to a mutant sequence having a SNP in the gene of interest;
   flowing an analyte with a fluorescent label over the planar waveguide, wherein the analyte comprises at least a portion of the gene of interest;
   detecting binding of the analyte to one or more wildtype probes of said plurality of wildtype probes and binding of the analyte to one or more SNP probes of said plurality of SNP probes by detecting fluorescent changes of the fluorescent label of the analyte, wherein the binding of the analyte to said one or more wildtype probes and the binding of the analyte to said one or more SNP probes cause the fluorescent changes of the fluorescent label of the analyte;
   comparing hybridization rates of the analyte binding to said one or more SNP probes with hybridization rates of the analyte binding to said one or more wildtype probes under hybridization conditions, wherein said SNP is detected in said gene of interest when the hybridization rate of the binding of the analyte to one wildtype probe from said one or more wildtype probes is significantly lower than the hybridization rate of the binding of the analyte to one SNP probe from said one or more SNP probes and the one wildtype probe from said one or more wildtype probes and the one SNP probe from one or more SNP probes differ by only one base.

2. The method of claim 1, wherein said detecting the fluorescent changes occurs in real-time.

3. The method of claim 1, wherein said one or more wildtype probes and said one or more SNP probes are probes specific for a KVLQT 1 gene and the at least a portion of the gene of interest is at least a portion of said KVLQT 1 gene.

4. The method of claim 3, wherein at least one of said one or more SNP probes is specific for position 760 of the nucleotide sequence in exon 3 of human KVLQT 1 gene, and detects a change from guanine to adenine at position 760 of the nucleotide sequence in exon 3 of said human KVLQT 1 gene.

5. The method of claim 1, wherein the analyte is a DNA sample or a polymerase chain reaction (PCR) product.

6. The method of claim 1, further comprising:
   differentiating the hybridization rates of the analyte binding to said one or more SNP probes from the hybridization rates of the analyte binding to said one or more wildtype probes by altering said hybridization conditions.

7. A method of detecting a single nucleotide polymorphism (SNP) in a KVLQT 1 gene comprising:

immobilizing on a planar waveguide a plurality of wildtype probes complementary to a KVLQT 1 gene or a region thereof, and a plurality of SNP probes complementary to a mutant sequence having a SNP in said KVLQT 1 gene, wherein the wildtype and SNP probes are 15-25 nucleotides in length;

flowing an analyte with a fluorescent label over the planar waveguide, wherein the analyte comprises a DNA sample from an individual;

detecting binding of the analyte to the one or more wildtype probes of said plurality of wildtype probes and binding of the analyte to the one or more SNP probes of said plurality of SNP probes by detecting fluorescent changes of the fluorescent label of the analyte, wherein the binding of the analyte to said one or more wildtype probes and the binding of the analyte to said one or more SNP probes cause the fluorescent changes of the fluorescent label of the analyte; and comparing the hybridization rates of the analyte binding to said one or more SNP probes with the hybridization rates of the analyte binding to said one or more wildtype probes under hybridization conditions, wherein said SNP is detected in said KVLQT1 gene when the hybridization rate of the binding of the analyte to one wildtype probe from said one or more wildtype probes is significantly lower than the hybridization rate of the binding of the analyte to one SNP probe from said one or more SNP probes and the one wildtype probe from said one or more wildtype probes and the one SNP probe from said one or more SNP probes differ by only one base.

8. The method of claim 7, wherein the analyte is a PCR product.

* * * * *

UNITED STATES PATENT AND TRADEMARK OFFICE
CERTIFICATE OF CORRECTION

| | |
|---|---|
| PATENT NO. | : 7,811,754 B2 |
| APPLICATION NO. | : 10/941289 |
| DATED | : October 12, 2010 |
| INVENTOR(S) | : James N. Herron et al. |

It is certified that error appears in the above-identified patent and that said Letters Patent is hereby corrected as shown below:

IN THE SPECIFICATION

In column 1, lines 17-20, replace "The research supporting this invention was partially funded by National Institute of Health Grant HL32132. The United States Government may have some right in this invention." with -- This invention was made with government support under HL032132 awarded by National Institutes of Health. The government has certain rights in this invention. --

Signed and Sealed this
Twenty-fifth Day of August, 2015

Michelle K. Lee
*Director of the United States Patent and Trademark Office*

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial
<220> FEATURE:
<223> OTHER INFORMATION: The T3 RNA polymerase promoter

<400> SEQUENCE: 1
aattaaccct cactaaaggg                                                 20

<210> SEQ ID NO 2
<211> LENGTH: 20
<212> TYPE: DNA
<213> ORGANISM: Artificial
<220> FEATURE:
<223> OTHER INFORMATION: sequence from exon 4 of the PSA gene

<400> SEQUENCE: 2
ggggcaaaag cacctgctcg                                                 20

<210> SEQ ID NO 3
<211> LENGTH: 20
<212> TYPE: DNA
<213> ORGANISM: Artificial
<220> FEATURE:
<223> OTHER INFORMATION: Hybridization probe derived from cDNA sequence
      of the PSA gene

<400> SEQUENCE: 3
cgagcaggtg cttttgcccc                                                 20

<210> SEQ ID NO 4
<211> LENGTH: 19
<212> TYPE: DNA
<213> ORGANISM: Artificial
<220> FEATURE:
<223> OTHER INFORMATION: Derived from the cDNA sequence of hGK2

<400> SEQUENCE: 4
ccacaagtgt ctttaccac                                                  19

<210> SEQ ID NO 5
<211> LENGTH: 21
<212> TYPE: DNA
<213> ORGANISM: Artificial
<220> FEATURE:
<223> OTHER INFORMATION: Capture probe for the G760A polymorphism in
      exon 3 of KVLQT1
```

```
<400> SEQUENCE: 5
atgaagacca cggagcccag g                                              21

<210> SEQ ID NO 6
<211> LENGTH: 21
<212> TYPE: DNA
<213> ORGANISM: Artificial
<220> FEATURE:
<223> OTHER INFORMATION: Wild-type analyte for G760A polymorphism

<400> SEQUENCE: 6
cctgggctcc gtggtcttca t                                              21

<210> SEQ ID NO 7
<211> LENGTH: 21
<212> TYPE: DNA
<213> ORGANISM: Artificial
<220> FEATURE:
<223> OTHER INFORMATION: G760A analyte for the A polymorphism in exon 3
      of the KVLQT1 gene

<400> SEQUENCE: 7
cctgggctcc atggtcttca t                                              21

<210> SEQ ID NO 8
<211> LENGTH: 10
<212> TYPE: DNA
<213> ORGANISM: Artificial
<220> FEATURE:
<223> OTHER INFORMATION: Capture Probe

<400> SEQUENCE: 8
ggagcccagg                                                           10

<210> SEQ ID NO 9
<211> LENGTH: 21
<212> TYPE: DNA
<213> ORGANISM: Artificial
<220> FEATURE:
<223> OTHER INFORMATION: Analyte probe

<400> SEQUENCE: 9
cctgggctcc gtggtcttca t                                              21

<210> SEQ ID NO 10
<211> LENGTH: 21
<212> TYPE: DNA
<213> ORGANISM: Artificial
<220> FEATURE:
<223> OTHER INFORMATION: Analyte probe

<400> SEQUENCE: 10
cctgggctcc atggtcttca t                                              21

<210> SEQ ID NO 11
<211> LENGTH: 21
<212> TYPE: DNA
<213> ORGANISM: Artificial
<220> FEATURE:
<223> OTHER INFORMATION: Analyte probe

<400> SEQUENCE: 11
cctgggctcc ctggtcttca t                                              21

<210> SEQ ID NO 12
```

```
<211> LENGTH: 21
<212> TYPE: DNA
<213> ORGANISM: Artificial
<220> FEATURE:
<223> OTHER INFORMATION: Analyte probe

<400> SEQUENCE: 12
cctgggctcc ttggtcttca t                                              21

<210> SEQ ID NO 13
<211> LENGTH: 5
<212> TYPE: DNA
<213> ORGANISM: Artificial
<220> FEATURE:
<223> OTHER INFORMATION: Sequencing probe
<220> FEATURE:
<221> NAME/KEY: misc_feature
<222> LOCATION: (2)..(5)
<223> OTHER INFORMATION: n is any nucleotide

<400> SEQUENCE: 13 cnnnn                                                                5

<210> SEQ ID NO 14
<211> LENGTH: 5
<212> TYPE: DNA
<213> ORGANISM: Artificial
<220> FEATURE:
<223> OTHER INFORMATION: Sequencing probe
<220> FEATURE:
<221> NAME/KEY: misc_feature
<222> LOCATION: (2)..(5)
<223> OTHER INFORMATION: n is any nucleotide

<400> SEQUENCE: 14 tnnnn                                                                5

<210> SEQ ID NO 15
<211> LENGTH: 5
<212> TYPE: DNA
<213> ORGANISM: Artificial
<220> FEATURE:
<223> OTHER INFORMATION: Sequencing probe
<220> FEATURE:
<221> NAME/KEY: misc_feature
<222> LOCATION: (2)..(5)
<223> OTHER INFORMATION: n is any nucleotide

<400> SEQUENCE: 15 gnnnn                                                                5

<210> SEQ ID NO 16
<211> LENGTH: 5
<212> TYPE: DNA
<213> ORGANISM: Artificial
<220> FEATURE:
<223> OTHER INFORMATION: Sequencing probe
<220> FEATURE:
<221> NAME/KEY: misc_feature
<222> LOCATION: (2)..(5)
<223> OTHER INFORMATION: n is any nucleotide

<400> SEQUENCE: 16 annnn                                                                5

<210> SEQ ID NO 17
<211> LENGTH: 5
<212> TYPE: DNA
<213> ORGANISM: Artificial
```

-continued

```
<220> FEATURE:
<223> OTHER INFORMATION: nondegenerate sequencing probe

<400> SEQUENCE: 17 cacca                                                                    5

<210> SEQ ID NO 18
<211> LENGTH: 5
<212> TYPE: DNA
<213> ORGANISM: Artificial
<220> FEATURE:
<223> OTHER INFORMATION: nondegenerate sequencing probe

<400> SEQUENCE: 18 tacca                                                                    5

<210> SEQ ID NO 19
<211> LENGTH: 5
<212> TYPE: DNA
<213> ORGANISM: Artificial
<220> FEATURE:
<223> OTHER INFORMATION: nondegenerate sequencing probe

<400> SEQUENCE: 19 gacca                                                                    5

<210> SEQ ID NO 20
<211> LENGTH: 5
<212> TYPE: DNA
<213> ORGANISM: Artificial
<220> FEATURE:
<223> OTHER INFORMATION: nondegenerate sequencing probe

<400> SEQUENCE: 20 aacca                                                                    5
```